(12) United States Patent
Clement et al.

(10) Patent No.: US 9,828,333 B2
(45) Date of Patent: Nov. 28, 2017

(54) COMPOUNDS FOR THE TREATMENT OF INFLUENZA

(71) Applicant: CHRISTIAN-ALBRECHTS-UNIVERSITAT ZU KIEL, Kiel (DE)

(72) Inventors: Bernd Clement, Kiel (DE); Joscha Kotthaus, Kiel (DE); Jurke Kotthaus, Kiel (DE); Dennis Schade, La Jolla, CA (US)

(73) Assignee: CHRISTIAN-ALBRECHTS-UNIVERSITAT ZU KIEL (DE)

( * ) Notice: Subject to any disclaimer, the term of this patent is extended or adjusted under 35 U.S.C. 154(b) by 0 days.

(21) Appl. No.: 14/354,654

(22) PCT Filed: Oct. 29, 2012

(86) PCT No.: PCT/EP2012/071382
§ 371 (c)(1),
(2) Date: Apr. 28, 2014

(87) PCT Pub. No.: WO2013/060889
PCT Pub. Date: May 2, 2013

(65) Prior Publication Data
US 2014/0288312 A1 Sep. 25, 2014

(30) Foreign Application Priority Data
Oct. 28, 2011 (DE) .................... 10 2011 117 128

(51) Int. Cl.
| | | |
|---|---|---|
| *C07C 235/68* | (2006.01) | |
| *C07C 231/12* | (2006.01) | |
| *A61K 31/165* | (2006.01) | |
| *A61K 31/192* | (2006.01) | |
| *A61K 31/609* | (2006.01) | |
| *C07C 275/14* | (2006.01) | |
| *C07C 279/16* | (2006.01) | |
| *C07D 263/06* | (2006.01) | |

(52) U.S. Cl.
CPC .......... *C07C 235/68* (2013.01); *C07C 231/12* (2013.01); *C07C 275/14* (2013.01); *C07C 279/16* (2013.01); *C07D 263/06* (2013.01); C07C 2601/16 (2017.05)

(58) Field of Classification Search
CPC ..... C03C 25/40; C03C 17/30; C08G 59/5066; C07C 2/868; C07C 321/00; C07C 235/68; C07C 231/12; A61K 31/165; A61K 31/192; A61K 31/609
USPC ............ 548/955, 215; 560/46; 514/166, 163
See application file for complete search history.

(56) References Cited

U.S. PATENT DOCUMENTS

| 5,763,483 A | 6/1998 | Bischofberger et al. |
| 5,952,375 A | 9/1999 | Bischofberger et al. |
| 2003/0044457 A1 | 3/2003 | Faour et al. |

FOREIGN PATENT DOCUMENTS

| WO | WO9914185 A1 | 3/1999 |
| WO | WO 2009029888 A2 * | 3/2009 |
| WO | WO2009029888 A2 | 3/2009 |
| WO | WO2010/075636 A1 | 7/2010 |
| WO | WO 2011123856 A1 * | 10/2011 |
| WO | WO2011123856 A1 | 10/2011 |

OTHER PUBLICATIONS

Liu, Kung-Cheng, P. Lee, S. Wang, Y. Cheng, J. Fang, and C. Wong "Intramolecular ion-pair prodrugs of zanamivir and guanidine-oseltamivir", Bioorganic & Medicinal Chemistry (2011), 19, pp. 4796-4802.*
Du, Q., R. Huang, Y. Wei, Z. Pang, L. Du, and K. Chou "Fragment-Based Quantitative Structure-Activity Relationship (FB-QSAR) for Fragment-Based Drug Design" Journ. Comput. Chem. (2009), 30(2), pp. 295-304.*
Hanessian, S., J. Wang, D. Montgomery, V. Stoll, K. Stewart, W. Kati, C. Maring, D. Kempf, C. Hutchins, and W. Laver "Design, Synthesis, and Neuraminidase Inhibitory Activity of GS-4071 Analogues that Utilize a Novel Hydrophobic Paradigm" Bioorg. & Med. Chem. Letters (2002), 12: pp. 3425-3429.*
Kung-Cheng Liu et al: "Intramolecular ion-pair prodrugs of zanamivir and guanidine-oseltamivir", Bioorganic & Medicinal Chemistry, Pergamon, GB, Bd. 19, Nr. 16, 27. Jun. 27, 2011.
Williams M.A. et al. "Structure-activity relationships of carbocyclic influenza neuraminidase inhibitors", Bioorganic & Medicinal Chemistry Letters, Pergamon, Elsevier Science, GB, Bd. 7, Nr. 14. Jul. 22, 1997.
Kim C.U. et al: "Structure-activity relationship studies of novel carbocyclic influenza neuraminidase inhibitors", Journal of Medicinal Chemistry, American Chemical Society, US, Bd. 41, Nr. 14, 9. Jun. 9, 1998.
Jiun-Jie Shie et al.: "Synthesis of Tamiflu and its Phosphonate Congeners Possessing Potent Anti-Influenza Activity", Journal of the American Chemical Society, Bd. 129, Nr. 39. Oct. 1, 2007.
International Preliminary Report on Patentabliity for International (PCT) Patent Application No. PCT/EP2012/071382 dated Apr. 29, 2014, 10 pages.

* cited by examiner

*Primary Examiner* — Matthew Coughlin
*Assistant Examiner* — Sagar Patel
(74) *Attorney, Agent, or Firm* — Sheridan Ross P.C.

(57) ABSTRACT

The invention relates to oseltamivir derivatives as influenza neuraminidase inhibitors for treating influenza infections and to a method for producing said compounds.

13 Claims, 7 Drawing Sheets

COMPOUNDS FOR THE TREATMENT OF INFLUENZA

CROSS REFERENCE TO RELATED APPLICATIONS

This application is a national stage application under 35 U.S.C. 371 and claims the benefit of PCT Application No. PCT/EP2012/071382 having an international filing date of Oct. 29, 2012, which designated the United States, which PCT application claimed the benefit of German Application No. 10 2011 117 128.6 filed Oct. 28, 2011, the disclosure of each of which are incorporated herein by reference.

The present invention relates to novel inhibitors of neuraminidase for the treatment of influenza (flu), and methods for their preparation.

Influenza represents a serious viral infection of the respiratory tract. Alone in the USA it is believed that between 10% and 20% of the population are annually being infected with this virus. According to WHO, this virus is responsible for the disease of 3 to 5 million people and 250.000 to 500.000 deaths per year, caused either directly by the virus or by secondary infections. By irregularly occurring epidemics or pandemics, the infection levels as well as the death counts are significantly increased. In the last century three major influenza pandemics, a H1N1 virus in the years 1918-19 ("Spanish flu"), a H2N2 virus in 1957 and an H3N2 virus in 1968 have cumulatively caused approximately 50 million deaths. The "Spanish flu" represents the most severe pandemic so far, which had caused the deaths of approximately 20 million people in just the first year. The last pandemic took place in 2009 and was known as the "Mexico flu" (H1N1, "pig flu"), but in terms of number of deaths caused, its course has been relatively harmless. However, especially the highly pathogenic "avian flu virus" (H5N1) has caused in the last years reasons of concern, among others because of the easy transmission from animal to human.

Currently, there are two main (and approved) therapeutic approaches to treat the flu or to prevent an infection:
(1) Vaccination
(2) The use of anti-viral active ingredients:
   a. M2 channel blockers, adamantane derivatives (amantadine, rimantadine)
   b. neuraminidase inhibitors However, neuraminidase inhibitors have significant advantages over the M2 channel blockers:
(1) a wide range of antiviral efficacy, as it is efficacious against influenza A and B. The adamantane derivatives are only efficacious against influenza A;
(2) a less strong induction of viral resistance mechanisms;
(3) better tolerability;
(4) better efficacy in reducing respiratory events.

The influenza virus is composed of an outer membrane surrounding the nucleocapsid. The glycoproteins hemagglutinin and neuraminidase are located on this outer membrane. After the virus has infected the cells and the virus replication has been initiated, new virus particles, so called virions, which are coated with sialic acid, are formed. As long as the sialic acid is bound to the virions, they aggregate with the hemagglutinin residues of other virions. These virion aggregations are no longer able to penetrate and infect other cells. Therefore, one of the functions of the neuraminidase is the cleavage of sialic acid residues from the virions, so that they can freely circulate in the body and infect other cells. Thus, the use of neuraminidase inhibitors represents a therapeutic approach in the treatment of influenza.

Meanwhile, some very potent neuraminidase inhibitors have been developed, such as zanamivir, oseltamivir and peramivir, which received pharmaceutical approval for the treatment of influenza.

In the field of neuraminidase inhibitors a lot of research and development work has been done in order to identify potential new active ingredients. Besides the development of new lead structures, numerous approaches have been followed, which aimed to optimize or modify known structures of oseltamivir and zanamivir. The common goal of all pursuits has always been to obtain compounds with either improved efficacy or bioavailability. In doing so, it is not possible to develop a compound which fully meets both criteria. However, a variety of modifications for the oseltamivir and zanamivir were described, which also lead to highly efficacious compounds against influenza. An overview of the already described modifications is given below:

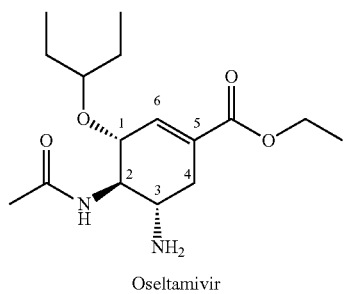 [SMILES: CCOC(=O)C1=C[C@@H](OC(CC)CC)[C@H](NC(C)=O)[C@@H](N)C1]

Oseltamivir

Position 1:

Many studies refer to the modification of the isopentyl side chain. By now, many modifications are known, which help decrease or increase the lipophilicity through the modified side chains and hence only slightly influence the affinity to neuraminidase.[1] In addition, it could be shown that a hydroxylation can be done at each position of the isopentyl chain.[2] Based on the structurally similar zanamivirs it was shown that variously substituted aliphatic radicals, as well as various cyclic side chains (hydroxylated and unhydroxylated) can be accepted on this position.[3] Li et al. extended this approach with the rational design of 46 oseltamivir analogous compounds and showed that a substitution in 1 position makes sense to increase the affinity to neuraminidase. Also in this study different substituents—both of aromatic and aliphatic nature—could be identified. Furthermore, the oxygen could be replaced by a nitrogen.[4] These data demonstrate that the structural requirements in this position in the molecule are relatively non-specific and various structures are accepted. Many other active derivatives of oseltamivir can thus be represented by modifying the isopentyl function and can be obtained the described procedures according to the invention in the following.

Position 4:

The modification of the 4-position of oseltamivir was, for instance, assessed by Wang et al.[6] It was shown that a substitution in this position is possible, in order to optimize the neuraminidase affinity. The substituents were linked to the cyclohexene backbone via carbon, oxygen or nitrogen respectively.

Position 5:

In this position various modifications are also possible. Therefore, it could be shown, for instance, that the carboxyl function can be replaced by other analogous functions (phosphonic acid, phosphonic acid ester, phosphonic acid amides etc.), without losing its efficaciousness.[7,8] Replacement of the carboxyl carbon by a sulfur to the corresponding sulfonic acid derivatives is also conceivable.

Position 6 and Backbone:

Further modifications relate to the cyclohexene backbone of oseltamivir. Various research groups were concerned with replacing this central structural feature by other structures, whereby nothing had been changed on the cyclic structure of the element. It was found that aromatic systems as well as 5-membered ring systems can have similar efficacies.[9,10] In addition, there were various aliphatic substitutions in 6 positions tested and their affinity for neuraminidase shown. Also conceivable is the use of hetero atoms in the ring system, as done in zanamivir. Thus, the modifications in the backbone demonstrate that not only the size of the central structural element can be varied, but also that the double bond in the cyclohexene of the oseltamivir is not essential. Variations in both the number and the position of the double bonds result in potent neuraminidase inhibitors.[10,11]

The great development efforts in the field of neuraminidase inhibitors development led to the identification of numerous oseltamivir analogous structures, which have an efficacy similar to oseltamivir. In terms of their overall properties, however, none of these derivatives is superior to oseltamivir, so that none of these analogues have been approved as an active ingredient.

Crucial for the success of a therapeutic agent is its pharmacokinetic profile, which is being influenced by solubility, the ability to activate potential prodrugs into their active forms, as well as the formation of protein bonds. Equally important is its stability under physiological conditions.

Of decisive importance is also the oral bioavailability of a therapeutic agent, medicine or drug, which indicates the extent to which an active ingredient is absorbed after oral administration. Oral administration is the easiest one to use, compared to other forms of administration. For example, sterility, which is required during infusion or injection, is not necessary. In addition, the dosage and application are much easier than in case of an inhaled medicament form.

Zanamivir and oseltamivir are currently approved in Germany for the treatment of influenza. While there is already an oral dosage form available for oseltamivir (Tamiflu®), the use of zanamivir is only inhalatively possible (Relenza®), since the bioavailability after oral administration is only 2%. In addition, in other countries peramivir is approved as an emergency drug for intravenous administration in the event of a pandemic. Laninamivir (Inavir®) was recently approved for the inhalation therapy of influenza in Japan.

In the event of a pandemic, the oral dosage forms seem to have an advantage over the inhalative or intravenous dosage forms.

A significant problem of the anti-influenza drugs is the rapid mutation of the influenza viruses, especially the viral major antigens (hemagglutinin and neuraminidase), so that they rapidly develop resistance against the existing drugs. This mutation is particularly pronounced in influenza A viruses. It may come to a sudden so-called "antigenic shift", due to which the annual (seasonal) adjustment of vaccines against influenza is required. In particular, the increased incidence of oseltamivir resistance against A(H1N1) with the H274Y mutation in the recent years is a cause for concern. Furthermore, next to some known mutations, further new resistance mechanisms have been discovered.

Should oseltamivir (Tamiflu®) be inefficacious against further resistance of the virus, a valuable quantity of the orally administered substance efficacious against influenza is lost.

Therefore, an objective of the invention is, starting from the oseltamivir structure, to find neuraminidase inhibitors that are also efficacious against oseltamivir-resistant virus strains.

Furthermore, an objective of the invention is to provide neuraminidase inhibitors, which exhibit an improved pharmacokinetic profile.

Moreover, an objective of the invention is to provide neuraminidase inhibitors, which have a good bioavailability.

The objective is achieved through the embodiments characterized in the claims and present description. The subclaims and examples show advantageous elaborations of the invention.

In one partial aspect, the objective of the invention is achieved by influenza neuraminidase inhibitors according to the general structural formula:

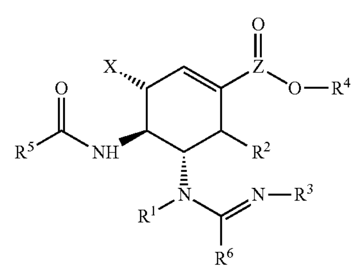

as well as pharmaceutically acceptable salts, solvates, R/S enantiomers, or prodrugs thereof, wherein $R^{1,4,5}$ may be identical or different and is hydrogen, a branched or unbranched, saturated or unsaturated, substituted or unsubstituted hydrocarbon chain having a chain length of 1 to 12, $R^2$ is H or substituents such as, for example, as they have been described in Wang et al.[6] or Park and Jo (Park and Jo, Eur. J. Med. Chem. 45 (2010), 536-541) and their disclosure has been incorporated by use in the preceding description, are especially selected from a group consisting of

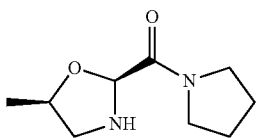

R² = Carbon-/Oxygen-/Nitrogen-Linker
(Wang et al.)
CH₂—NH₂(CONH₂)
(Park und Jo)

CH₂OH, CH₂NH₂, CH₂CONH₂, CH₂CH₂CONH₂, a branched or unbranched, saturated or unsaturated, substituted or unsubstituted hydrocarbon chain having a chain length of 1 to 12,
$R^3$ is H, OH, $OR^1$, $OCOOR^1$ or $COOR^1$,
$R^6$ is H, $R^1$, $NH_2$, $NHR^1$, $N(R^1)_2$, $NHCOOR^1$,
X is $OR^1$, $SR^1$, $NHR^1$ or $N(R^1)_2$,
Z represents C, S, SO, P, PO, and
wherein optional substituents for $R^1$ are selected from a group consisting of fluorine, chlorine, bromine and iodine, oxygen, sulfur, alkoxy, acyloxy, hydroxyl, mercapto, cyano, nitro and thio alkoxy group, or a functionality which is blocked with a protecting group, for the treatment of influenza infections.

In a preferred aspect, the invention relates to influenza neuraminidase inhibitor compounds according to the present invention, wherein the inhibitor amidoxime amidoxime (3R,4R,5S)-4-acetamido-5-[N—(N'-hydroxy)acetimidamido]-3-(1-ethylpropoxy)cyclohex-1-en-1-carboxylic acid ethyl ester, or hydroxyguanidine (3R,4R,5S)-4-acetamido-5-[N—(N'hydroxy)-guanidino]-3-(1-ethylpropoxy)cyclohex-1-en-1-carboxylic acid ethyl ester as well as pharmaceutically acceptable salts, solvates or prodrugs thereof are for the treatment of influenza infections.

Based on oseltamivirs' basic structure, the compounds according to the invention provide new inhibitors of the influenza neuraminidase.

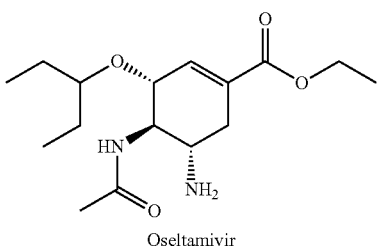 [SMILES: CCOC(=O)C1=C[C@@H](OC(CC)CC)[C@H](NC(C)=O)[C@@H](N)C1]

Oseltamivir

In a further aspect, the invention relates to a method for preparing a compound according to the present invention as described above, comprising the reaction of oseltamivir according to the general structural formula:

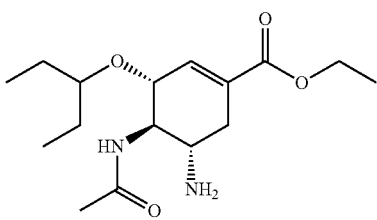 [SMILES: CCOC(=O)C1=C[C@@H](OC(CC)CC)[C@H](NC(C)=O)[C@@H](N)C1]

or a derivative thereof which comprises at least the following step:

Reaction of oseltamivirs with a acyl hydroximoyl chlorid, in organic solvents at room temperature.

Preferred is a method, wherein the organic solvent is dichloromethane. In a particularly preferred aspect, the method according to the invention refers to the amidoxime compound with $R^3$=OH according to the general structural formula mentioned above.

As an optional step, a transfer of the ethyl ester function ($R^4$=CH₂CH₃, Z=C) in a carboxyl function ($R^4$=H, Z=C) can take place, through treatment with hydroxides in alcoholic solutions.

Thio amidinium salts are preferred as an amidation reagent. The S-naphthyl-methyl-acet-amidinium-bromide was preferably used.

As an alcohol, organic compounds having a saturated or unsaturated, branched or unbranched carbon chain of length C1 to C6 are suitable, particularly preferred are alcohols, which have a saturated branched or unbranched carbon chain of length C1 to C6. Most preferably, the alcohols methanol, ethanol, propanol, butanol, iso-propanol and tert-butanol are used. For the purposes of the present invention, alcoholic solution means that herein one or more alcohols, according to the definition above, are included.

The preparation of amidoximes ($R^3$=OH) according to the invention is done according to the invention by a method that includes at least the following step: Reaction of oseltamivir with a hydroximoyl chloride (e.g. acetyl hydroximoyl chloride), in organic solvents (e.g. dichloromethane) at room temperature.

Organic solvents are known to the skilled person and include in addition to dichlormethane, for example, chloroform, acetone, acetonitrile, methanol, etc.

Moreover, the present invention relates to a method for preparing a compound according to the present invention comprising the reaction of oseltamivir (3R,4R,5S)-4-acetamido-5-amino-3-(1-ethylpropoxy)cyclohex-1-en-1-carboxylic acid ethyl ester or a derivative thereof which comprises at least one of the following steps (i) Reaction of oseltamivir with cyanogen bromide in an organic solvent at room temperature, (ii) Reaction of the cyanamide formed in with hydroxylamine in dioxane at room temperature.

Specifically, the present invention relates to a method as described above, wherein the compound is hydroxyguanidine $R^6$=NH₂, $NHR^1$ or $N(R^1)_2$ and $R^3$=OH according to the general structural formula above.

As already explained above, the modifications made according to the invention, as illustrated based on oseltamivir, and consequently the method according to the invention can also be applied to derivatives of oseltamivir, which, for example, have been modified at the residues discussed above such as oseltamivir derivatives already described in the state of the art, that consequently can be unequivocally recognized by the skilled person as equivalent embodiment of the present invention, illustrated in the examples.

For the representation of the neuraminidase inhibitors according to the invention, various synthetic strategies were pursued, which all together revealed a variety of very differently substituted oseltamivir derivatives. Examples of different synthetic routes, which lead to different active ingredients according to the invention, are shown in the following overview.

Overview of the synthesis of neuraminidase inhibitors.
A)
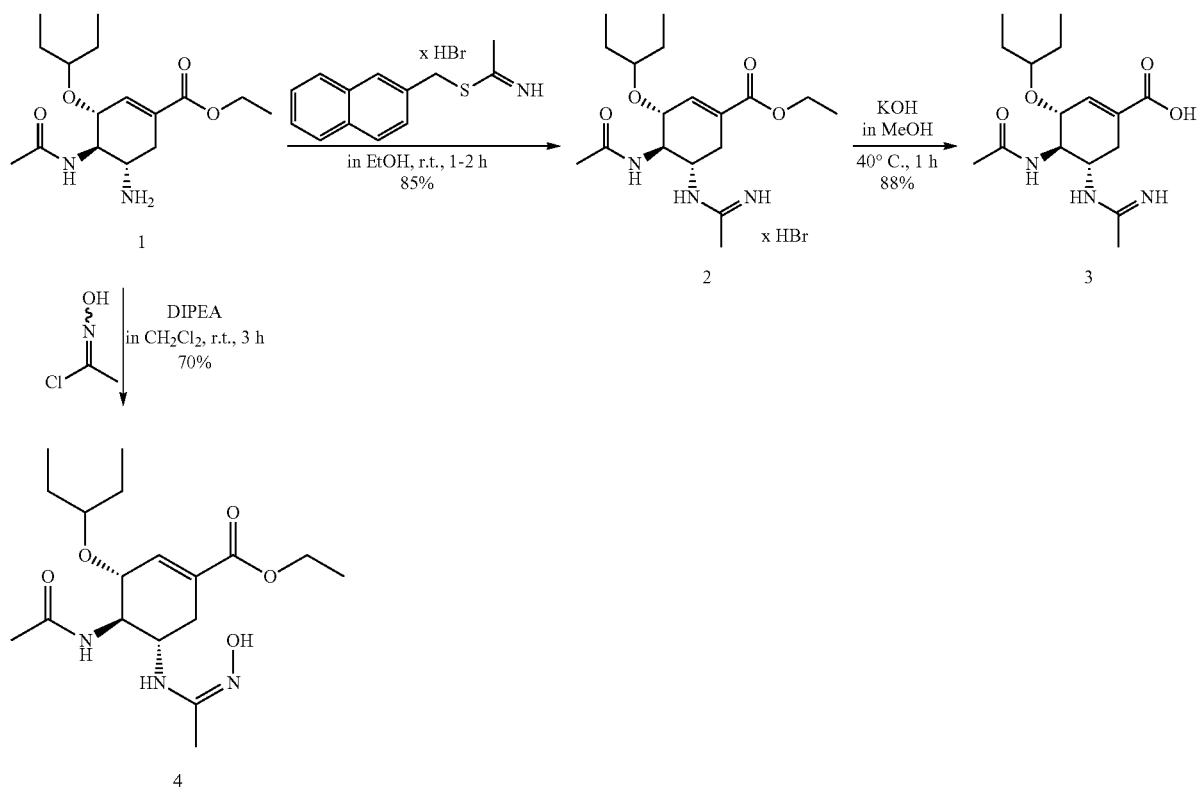
B)
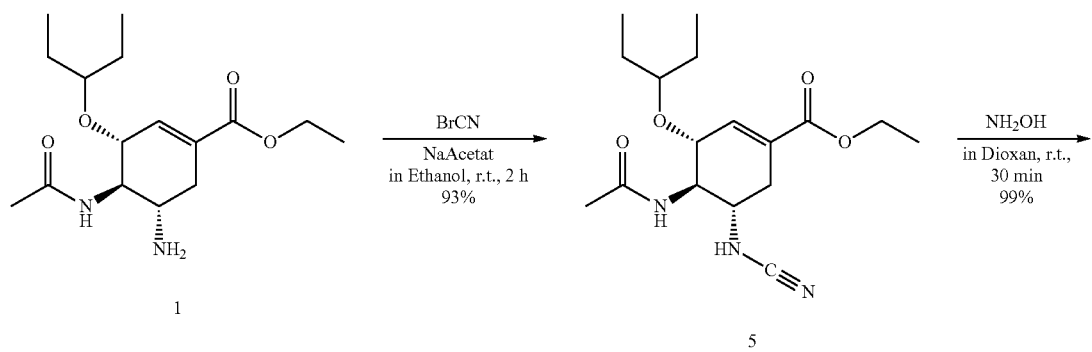
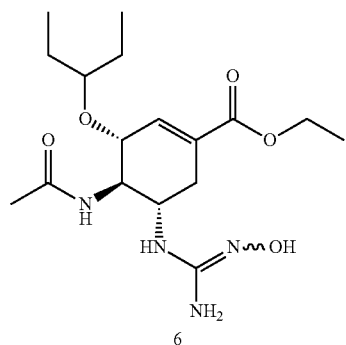

C)

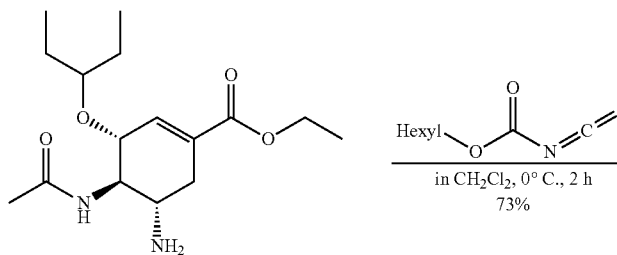

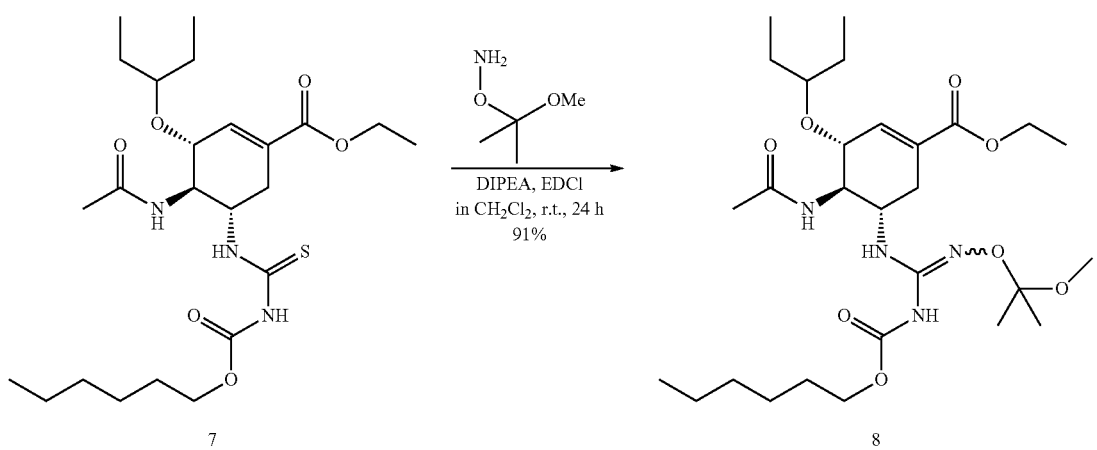

D)

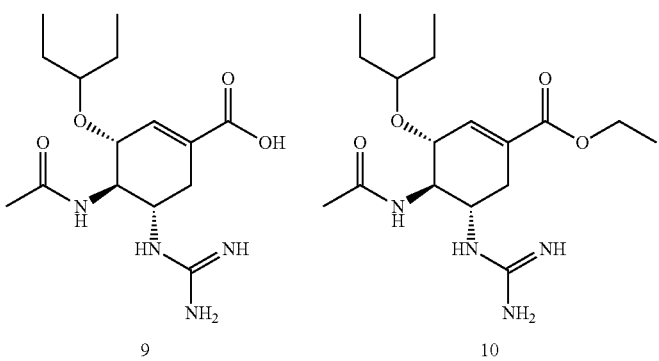

A) synthesis route of amidine-based oseltamivir derivative 3, as well as to the corresponding amidoxime 4;
B) synthesis route to hydroxyguanidine-based oseltamivir derivative 6;
C) synthesis route to further hydroxyguanidine-based oseltamivir derivatives (8);
D) structural formulas of oseltamivir-guanidine 9 and its ester prodrugs 10.

S-naphthyl-methyl-acet-amidinium-bromide was used as an amidation reagent for the representation of the amidines (2, 3) (see A). The use of other reagents for the preparation of amidines is also possible. By foregoing N-substitution of the oseltamivir and by choosing another thio amidinium salt, a variety of amidines are accessible in this way. Other known methods for establishing an amidine function can be used here. Amidoxime 4 was preferably represented by using acethydroximoyl chloride.

The synthesis of the guanidine-based compounds is shown under B). Two different concepts for establishing substituted and unsubstituted hydroxyguanidines were implemented hereby. Thus, the unsubstituted hydroxyguanidine 6 is accessible via the representation of the cyanamide 5. And very different O,N-substituted hydroxyguanidines (8) are representable via carbamoyl-substituted thiourea of type 7 (see C).

The oseltamivir—guanidine 9 and its ester prodrug 10 are also shown. The representation succeeded according to Shie et al. [Shie, J.; Fang, J.; Wang, S.; Tsai, K.; Shyun, Y.; Cheng, E.; Yang, A.; Hsiao, S.; Su, C.; Wong, C., Journal of American Chemical Society 2007, 129, 11892-93].

In a further aspect, the invention relates to providing new oseltamivir derivatives as well as appropriate solvates, salts, R/S enantiomers and/or prodrugs according to the general structural formula:

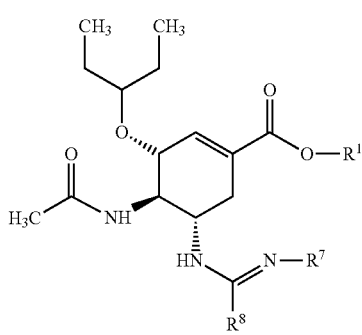

wherein
R¹ is H, a branched or unbranched, saturated or unsaturated, substituted or unsubstituted hydrocarbon chain having a chain length of 1 to 12, R⁷ is H or OH, R⁸ is H, R⁹, NH₂, NHR⁹, N(R⁹)₂ or NHCOOR¹,
R⁹ is a branched or unbranched alkyl radical having a chain length of 1 to 4 carbon atoms and
wherein possible substituents for R¹ and R⁹ are selected from the group consisting of fluorine, chlorine, bromine and iodine, oxygen, sulfur, alkoxy, acyloxy, hydroxyl, mercapto, cyano, nitro and thio alkoxy group, or a functionality which is blocked with a protecting group.

In one embodiment, the present invention does not relate to the compounds GS4116 and GS4109 described on page 648 in the publication by Li et al. Antimicrobial Agents and Chemotherapy 42 (1998), 647-653, in which, among others R' is H or CH₂CH₃, R⁷ is H and R⁸ is NH₂.

In a further embodiment, the present invention relates to compounds in which when R⁸ is NH₂, R⁷ is OH.

In a further embodiment, the present invention relates to compounds in which if R⁷ is H and R⁸ is NH₂, R¹ is not H or CH₂CH₃.

In a preferred embodiment, the invention relates to the compound amidoxime (3R,4R,5S)-4-acetamido-5-[N—(N'-hydroxy)acetimidamido]-3-(1-ethylpropoxy)cyclohex-1-en-1-carboxylic acid ethyl ester, or or hydroxyguanidine (3R, 4R,5S)-4-acetamido-5-[N—(N'hydroxy)-guanidino]-3-(1-ethylpropoxy)cyclohex-1-en-1-carboxylic acid ethyl ester and/or pharmaceutically acceptable salts, solvates, R/S enantiomers and/or prodrugs thereof.

In a preferred embodiment, the present invention relates to the compounds and neuraminidase inhibitors described above for use as a medicament, preferably for the treatment of influenza infections, wherein in one embodiment, the medicament according to the invention encompasses, as described in the publication by Li et al. Antimicrobial Agents and Chemotherapy 42 (1998), 647-653, the compounds GS4116 and GS4109 described on page 648, in which R¹ is H or CH₂CH₃, R⁷ is H and R⁸ is NH₂ according to the general structural formula above. Contrary to the statements in Li et al., the guanidine derivatives (3 and 9) according to the invention show a very good efficacy against influenza.

It has been shown in the experiments conducted according to the invention that the exchange of the amine function by an amidine or guanidine group can overturn existing influenza resistance mechanisms. The test data obtained in the experiments conducted according to the invention from various antiviral assays show that the amidine and guanidine derivatives are comparable potent against influenza A (H1N1) strains as oseltamivir and zanamivir, but additionally efficacious against an oseltamivir-resistant influenza A (H1N1) strain. They are also efficacious against various influenza A (H3N2) strains. In addition, the compounds according to the invention exhibit surprisingly low toxicity in cytotoxicity assays, good solubility, good activation in the active form as well as a very good stability under physiological conditions.

Table 1 shows the efficacy of the substances (3 and 9) according to the invention in the neuraminidase (NA) inhibition assay compared to zanamivir and oseltamivir. A detailed description of the test can be found in the description of the methods.

TABLE 1

Efficacy of the test and control substances in the NA inhibition assay

H3N2-subtype

50% inhibitory concentration (nM) with respect to

| Substance | Hong Kong/ 8/68 | Saxony/ 6/02 | Berlin/ 10/04 | Rhineland-Palatinate/ 3911/03 |
|---|---|---|---|---|
| Amidine active form 3 | 1.0 | 1.2 | 1.3 | 0.7 |
| Guanidine active form 9 | 1.1 | 1.3 | 1.0 | 0.5 |
| Zanamivir | 0.3 | 0.4 | 0.4 | 0.2 |
| Oseltamivir | 0.2 | 0.1 | 0.1 | 0.1 |

H1N1-subtype

50% inhibitory concentration (nM) with respect to

| Substance | A/Jena/ 5258/2009 | A/Jena/ 5555/09 | A/HH/ 1580/09 | A/ 342/2009 |
|---|---|---|---|---|
| Amidine active form 3 | 0.1 | 0.2 | 0.1 | 11.6 |
| Guanidine active form 9 | 0.1 | 0.3 | 0.1 | 2.6 |
| Zanamivir | 0.1 | — | — | 0.2 |
| Oseltamivir | 0.1 | 0.1 | 0.1 | resistant |

The values in Table 1 show that both 3 and 9 inhibit the NA activity of the eight tested influenza A viruses in the nanomolar concentration range. The determined IC50 values in the NA inhibition assay were roughly comparable to those of zanamivir and oseltamivir.

In contrast to oseltamivir, 3 and 9 are also efficacious against the oseltamivir-resistant isolate A/342/2009. The 50% inhibitory concentrations defined for this virus were 10-(9) or 50-fold (3) higher compared to zanamivir.

The antiviral efficacy is also evident in virus yield inhibition assay. The test results are shown in Table 2. The amidine active form (3) and the guanidine active form (9) reduced the titre of influenza virus A/Jena/5258/2009 in nanomolar concentration range to 90 respectively 95%. A detailed description of the test conditions is to be found in the description of the methods.

TABLE 2

Antiviral efficacy of the test substances in virus
yield inhibition assay with influenza A virus
in MDCK cells (Madin Darby canine kidney)

| Substance | 90% resp. 95%* inhibitory concentration (µM) with respect to | |
|---|---|---|
| | A/Jena/5258/2009 | A/342/2009 |
| Amidine active form 3 | 0.001 (0.011) | 16.0 (22.3) |
| Guanidine active form 9 | 0.002 (0.003) | 3.0 (14.2) |
| Zanamivir | 0.125 (0.219) | 1.5 (2.5) |
| Oseltamivir | 0.016 (0.021) | resistant |

*Values in parentheses

In the cpE inhibition assay there are also signs of the antiviral activity of the compounds according to the invention.

The replication of the virus used in the test leads to total destruction of the host cells, due to a highly pronounced cytopathic effect (cpE). By adding antiviral active substances (100 µl/well; 3 parallels/concentration, dilution factor 2), the virus-induced cpE can be selectively inhibited. In the test, substance-treated and untreated enclosed cell layers were vaccinated with a dose of virus, which lead to a complete cpE in untreated virus controls, 48 h after the infection.

TABLE 3

Antiviral efficacy of test substances in the cpE inhibition
assay with the influenza A virus in MDCK cells

| Substance | 50% inhibitory concentration (µM) with respect to | |
|---|---|---|
| | A/Jena/5258/2009 | A/342/2009 |
| Amidine active form 3 | 2.0 | 12.1 |
| Guanidine active form 9 | 1.1 | 4.1 |
| Zanamivir | >19.5 | 0.6 |
| Oseltamivir | 13.2 | resistant |

The amidine active form 3 and the guanidine active form 9 inhibited in the non-cytotoxic concentration range the cpE of influenza virus A/Jena/5258/2009 respectively A/342/2009, wherein the 50% inhibitory concentrations were set at 2.0 and 12.2 µM (derivative 3) respectively at 1.1 and 4.1 µM (derivative 9). A detailed description of the test conditions of the test is to be found in the description of the methods.

Another advantage of the compounds according to the invention is their low toxicity. In this regards, the amidine (3), as well as the guanidine active forms (9) were found to be non-toxic in the tested concentration range of 6.25 to 200 µg/ml within the cytotoxicity assay for the determination of the 50% cytotoxic dose ($CC_{50}$) of the test substances in MDCK (Madin Darby canine kidney) cell layers. A detailed description of the test conditions is be found in the description of the methods.

Another positive feature of the compounds according to the invention is their good stability, especially under physiological conditions. The tests showed that representative compounds are very stable within the pH range from 2 to 9 (FIG. 1). There has been no observed decomposition of the compound within the test period of 6 h for any of the compounds.

For the active forms 3 and 9, an additional stability test was conducted for 14 days, which showed that both substances are stable under physiological pH, both at 4° C. and at RT over the test period (FIG. 2). The storage stability in solution was determined at a concentration of 0.2 mg/ml. Therefor, a compound was dissolved in 50 mM $KH_2PO_4$ buffer, pH 7.4 respectively Aqua bidest and stored at RT (pH 7.4) or in a refrigerator at 4° C. (pH 7.4 respectively Aqua bidest) over the test period. The concentration of the active form was determined after 12 h, 1 d, 2 d, 4 d, 7 d and 14 d by HPLC.

Other tests with murine and human plasma showed that the ester functions (in all prodrugs, the ethyl ester of the carboxy function) are rapidly cleaved by plasma enzymes. The ester cleavage is an important step in the bio-activation, which could be substantiated by these incubations. The active forms 3 and 9 are not metabolized by plasma enzymes.

A particular advantage of the compounds according to the invention is their good solubility. Most of the compounds (2, 3, 6 and 10) are soluble at a concentration >50 mM, for all studied pH values (Table 4). In addition, it was found that all the substances are soluble more than 50 mM at a pH value of 2. Thus, it can be assumed that all compounds will solve very well in the acidic environment in the stomach. In addition, however, the less soluble substances (4, 9) are still more soluble than 20 mM, at all pH values. Thus, all compounds show very good solubility characteristics, which is a positive factor with respect to their later use as an active ingredient. Hence, for instance, in addition to an oral administration form, there are also liquid administration forms (injections, infusion), needed in the emergency medication.

TABLE 4

Solubility of the tested compounds at different pH values.

| Compound | pH value | maximum soluble concentration | |
|---|---|---|---|
| | | [mg/ml] | [mM] |
| 2 | 9.0 | >17.7 | >50 |
| | 7.4 | >17.7 | >50 |
| | 2.0 | >17.7 | >50 |
| 3 | 9.0 | >16.3 | >50 |
| | 7.4 | >16.3 | >50 |
| | 2.0 | >16.3 | >50 |
| 4 | 9.0 | 8.6 ± 0.7 | 23.3 ± 1.8 |
| | 7.4 | 8.6 ± 0.4 | 23.2 ± 1.2 |
| | 2.0 | >18.5 | >50 |
| 6 | 9.0 | >18.5 | >50 |
| | 7.4 | >18.5 | >50 |
| | 2.0 | >18.5 | >50 |
| 9 | 9.0 | 8.0 ± 0.1 | 24.6 ± 0.2 |
| | 7.4 | 8.6 ± 0.3 | 26.2 ± 1.1 |
| | 2.0 | >16.3 | >50 |
| 10 | 9.0 | >23.4 | >50 |
| | 7.4 | >23.4 | >50 |
| | 2.0 | >23.4 | >50 |

Another advantage of the compounds according to the invention is the fact that the compounds develop only very moderate plasma protein bindings. The conducted experiments showed that all tested compounds posses protein bindings of less than 40% (Table 5). The risk of clinically relevant medicament interaction increases only starting with protein bindings greater than 90%, thus clinically relevant interactions through protein bindings for the prodrugs, as well as for the active forms developed here are not to be expected.

TABLE 5

Detected protein bindings in a 4% albumin solution for the tested compounds. The values shown represent the average values of the determinations at three different concentrations.

| Compound | Protein binding [%] |
|---|---|
| 3 | 2.2 ± 1.5 |
| 9 | 0.4 ± 2.8 |
| 2 | 34.8 ± 8.8 |
| 10 | 30.1 ± 2.3 |
| 4 | 26.7 ± 2.5 |
| 6 | 37.5 ± 10.1 |

In addition, the protein binding of both active forms oseltamivir-amidine (3) and oseltamivir-guanidine (9) was examined in human plasma. Therefor, human plasma was used instead of the 4% albumin solution. There were protein bindings of 3.7±1.4% for compound 3 and 8.6±3.0% for compound 9 determined. The values are as expected somewhat higher than the values obtained with the 4% albumin solution and are to be traced back to the presence of other plasma proteins (e.g. $\alpha_1$-acidic glycoprotein) in addition to albumin.

Another particular advantage of the compounds according to the invention is the fact that, in this case, already established prodrug concepts can be used. The carboxylic acid is used in the conventional form as an ester. For the amidine and guanidine functions, the N-hydroxy-concept, likewise meanwhile established now, was used. The prodrug forms described are interesting also from the point of view of a sustained release of the active form after oral or parenteral administration.

For the prodrugs in vitro tests were conducted on stability, solubility and activation into the active form. The results showed that the compounds present a sufficient stability, very good solubility and that the activation into the active form takes place to a good extent through different enzyme preparations.

The activation of prodrugs into their active forms was determined in vitro by means of subcellular enzyme preparations. As enzyme preparations, 9000 g supernatants, microsomes and mitochondria were used from human and porcine liver tissues. The incubation mixtures consisted of 500 μM prodrug, 500 μM NADH, 1 U esterase and 0.3 mg enzyme preparation, dissolved together in 150 μl of 100 mM phosphate buffer pH 6.3. The incubation was carried out for 30 min at 37° C. in a shaking water bath. The incubation was terminated by adding 150 μl of acetonitrile. Subsequently, the samples were shaken for 10 min and the precipitated protein was centrifuged at 10,000 rpm for 15 min. The supernatant was measured by HPLC.

The conversion rates obtained are shown in Table 6.

The activation studies carried out in vitro showed that all developed prodrugs have been converted to the active form 3 and 9 (Table 4). That is, the ester cleavage takes place as it could be shown in the stability studies in human and murine plasma, and in addition, the reduction of the amidoxime respectively the N—OH-guanidine could be detected in these incubations. In summary, it can be stated that the compounds 2, 4, 6 and 10 are suitable prodrugs of the active forms 3 and 9. This study provides only the general proof that the bioactivation of the compounds takes place. The conversion rates should be significantly higher in vivo.

TABLE 6

Activation of the prodrug into the active form with subcellular enzyme preparations

| Enzyme preparation | Conversion rate [nmol/min/mg protein] | | | |
|---|---|---|---|---|
| | 2 | 4 | 8 | 10 |
| Human liver mitochondria | 0.56 ± 0.04 | 0.22 ± 0.16 | 1.74 ± 0.06 | 0.79 ± 0.04 |
| Pig liver mitochondria | 0.15 ± 0.01 | 0.51 ± 0.06 | 0.67 ± 0.02 | 0.21 ± 0.01 |
| Human liver 9000 g supernatant | 0.20 ± 0.02 | 0.56 ± 0.06 | 0.76 ± 0.09 | 0.32 ± 0.03 |
| Pig liver 9000 g supernatant | 0.42 ± 0.10 | 5.34 ± 0.15 | 1.53 ± 0.14 | 0.22 ± 0.01 |
| Human liver microsomes | 0.64 ± 0.01 | 2.30 ± 0.20 | 1.76 ± 0.05 | 1.06 ± 0.02 |
| Pig liver microsomes | 0.30 ± 0.11 | 7.51 ± 0.66 | 4.77 ± 0.13 | 0.22 ± 0.01 |

The enzymatic hydrolysis of the carboxylic acid ethyl ester was analysed in more detail in the prodrugs 2 and 10. Non-specific carboxyl esterases from pig liver were hereby used as enzyme source. The incubation mixtures contained 200 μM prodrug and 3 U esterase dissolved in 200 μl of 100 mM phosphate buffer pH 7.4. The incubation was carried out over a period of 60 min at 37° C. The samples were analysed every 15 min by HPLC.

The incubations showed that both prodrugs are activated by esterase to their respective active forms. The conversion rates were 0.83±0.14 nmole/min/mg protein (prodrug 2) and 1.35±0.15 nmol/min/mg protein (prodrug 10).

A particular advantage of the compounds according to the invention is their good bioavailability.

The newly developed neuraminidase inhibitors have been tested in an animal study on rats with respect to their oral bioavailability. All tested compounds show hereby that they are absorbed from the gastrointestinal tract, as well as metabolized into their active form. The metabolism of neuraminidase inhibitors 4 and 6 is shown for clarification.

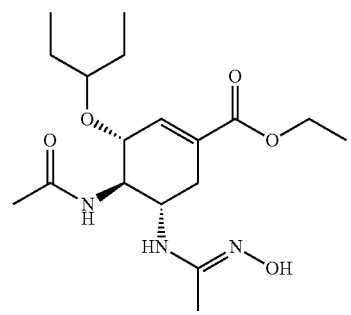

4

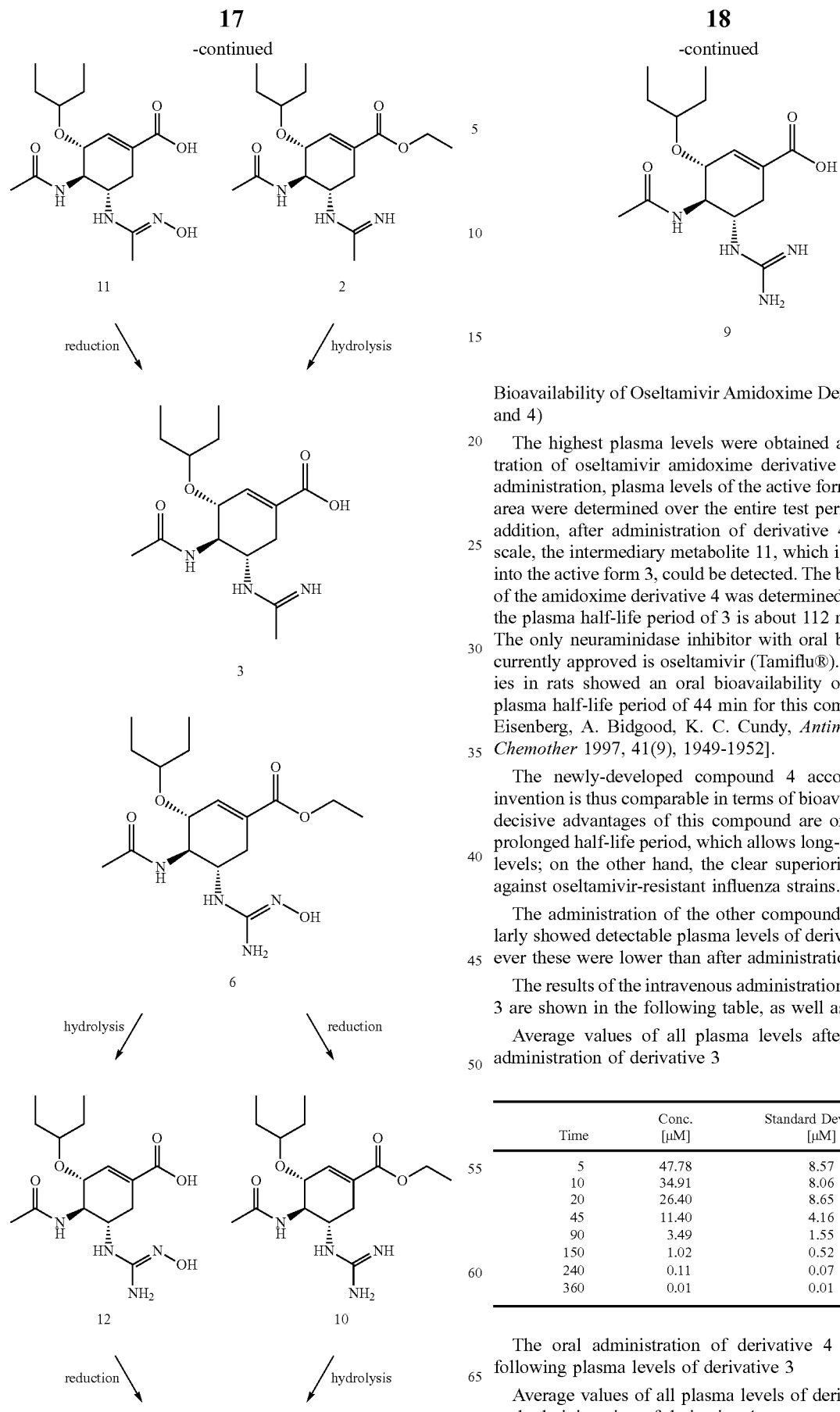

Bioavailability of Oseltamivir Amidoxime Derivatives (2, 3 and 4)

The highest plasma levels were obtained after administration of oseltamivir amidoxime derivative 4. After oral administration, plasma levels of the active form 3 in μmolar area were determined over the entire test period of 6 h. In addition, after administration of derivative 4 on a lower scale, the intermediary metabolite 11, which is metabolized into the active form 3, could be detected. The bioavailability of the amidoxime derivative 4 was determined to be 31.3%; the plasma half-life period of 3 is about 112 min (Table 2). The only neuraminidase inhibitor with oral bioavailability currently approved is oseltamivir (Tamiflu®). Animal studies in rats showed an oral bioavailability of 36% and a plasma half-life period of 44 min for this compound. [E. J. Eisenberg, A. Bidgood, K. C. Cundy, Antimicrob Agents Chemother 1997, 41(9), 1949-1952].

The newly-developed compound 4 according to the invention is thus comparable in terms of bioavailability. The decisive advantages of this compound are on one hand a prolonged half-life period, which allows long-acting plasma levels; on the other hand, the clear superiority in efficacy against oseltamivir-resistant influenza strains.

The administration of the other compounds (2, 3) similarly showed detectable plasma levels of derivative 3, however these were lower than after administration of 4.

The results of the intravenous administration of derivative 3 are shown in the following table, as well as in FIG. 3.

Average values of all plasma levels after intravenous administration of derivative 3

| Time | Conc. [μM] | Standard Deviation [μM] |
|---|---|---|
| 5 | 47.78 | 8.57 |
| 10 | 34.91 | 8.06 |
| 20 | 26.40 | 8.65 |
| 45 | 11.40 | 4.16 |
| 90 | 3.49 | 1.55 |
| 150 | 1.02 | 0.52 |
| 240 | 0.11 | 0.07 |
| 360 | 0.01 | 0.01 |

The oral administration of derivative 4 provided the following plasma levels of derivative 3

Average values of all plasma levels of derivative 3 after oral administration of derivative 4

| Time [min] | Conc. [μM] | Standard Deviation [μM] |
|---|---|---|
| 0 | 0.00 | 0.00 |
| 30 | 6.50 | 1.90 |
| 60 | 8.98 | 2.53 |
| 90 | 8.80 | 2.30 |
| 120 | 8.10 | 1.60 |
| 180 | 6.43 | 1.50 |
| 240 | 5.34 | 1.50 |
| 360 | 2.19 | 1.08 |

FIG. 4 shows the results graphically.

After oral administration of derivative 4, derivative 11 is detected as a metabolite. This can also be deduced from FIG. 5.

Average values of all plasma levels of intermediary metabolite 11 after oral administration of derivative 4

| Time [min] | Conc. [μM] | Standard Deviation [μM] |
|---|---|---|
| 0 | 0.00 | 0.00 |
| 30 | 7.22 | 1.77 |
| 60 | 2.68 | 1.23 |
| 90 | 2.16 | 0.86 |
| 120 | 1.96 | 0.63 |
| 180 | 0.85 | 0.41 |
| 240 | 0.49 | 0.18 |
| 360 | 0.13 | 0.15 |

The oral administration of derivative 3 leads to the following plasma levels; refer also to FIG. 6

Average values of all plasma levels of derivative 3 after oral administration of derivative 3

| Time [min] | Conc. [μM] | Standard Deviation [μM] |
|---|---|---|
| 0 | 0.00 | 0.00 |
| 30 | 1.63 | 0.11 |
| 60 | 1.59 | 0.18 |
| 90 | 1.50 | 0.12 |
| 120 | 1.25 | 0.11 |
| 180 | 0.61 | 0.04 |
| 240 | 0.30 | 0.03 |
| 360 | 0.04 | 0.00 |

The oral administration of derivative 2 leads to the following plasma levels refer also to FIG. 7

Average values of all plasma levels of derivative 3 after oral administration of derivative 2

| Time [min] | Conc. [μM] | Standard Deviation [μM] |
|---|---|---|
| 0 | 0 | 0 |
| 30 | 0.43 | 0.21 |
| 60 | 0.35 | 0.12 |
| 90 | 0.33 | 0.17 |
| 120 | 0.29 | 0.16 |
| 180 | 0.07 | 0.04 |
| 240 | 0.01 | 0.01 |
| 360 | 0.00 | 0.00 |

FIG. 8 and the following table show an overview of the results from the administration of the amidine-based neuraminidase inhibitors (2, 3 and 4).

TABLE 7

Pharmacokinetic parameters of amidine-based neuraminidase inhibitors

| Derivative | 3 | 3 | 4 | 2 |
|---|---|---|---|---|
| Administration | Iv | Oral | Oral | Oral |
| Rats (n) | 5 | 3 | 6 | 5 |
| MW [g/mol] | 325 | 325 | 369 | 434 (HBr) |
| Dose [mg/kg] | 10 | 50 | 50 | 50 |
| Dose (Equi) | 1 | 5 | 4.40 | 3.74 |
| AUC | 576.8 | 86.4 | 793.2 | 17.0 |
| $t_{max}$ [min] | — | 44.1 | 91.8 | 30.9 |
| $c_{max}$ [μg/ml] | — | 0.7 | 2.8 | 0.2 |
| MRT [min] | 35.2 | 112.0 | 206.8 | 90.8 |
| $t_{1/2}$ [min] | 38.5 | 40.7 | 111.7 | 37.8 |
| Bioavailability [%] | 100 | 3.0 | 31.3 | 0.8 |

AUC = area under the curve; $t_{max}$ = time, at which the maximum plasma level was measured. $c_{max}$ = maximum plasma concentration, which was determined; MRT = Mean Residence Time
$t_{1/2}$ = plasma half-life period; MRT (Mean Residence Time) is, similarly to the plasma half-life period $t_{1/2}$ a measure for the retention time of a substance in the body. It is a classical pharmacokinetic value, which is obtained by dividing the AUMC (area under the first moment curve) by AUC;

Bioavailability of Oseltamivir Hydroxyguanidine Derivatives (6, 9, 10)

Analysis of plasma samples provided, after administration of all tested derivatives, detectable plasma levels of derivative 9 over a period of 6 h. In comparison to the oseltamivir amidoxime derivatives (see a), the plasma levels determined were, however, significantly lower. The plasma concentrations of derivative 9 were determined in the three-digit nanomolar range and are thus by approximately a factor of 10 lower compared to derivative 4. After administration of derivative 6, the intermediary metabolite 12, which is metabolized into the active form 9, could be detected.

The bioavailability of the hydroxyguanidine derivative 6 was determined to be 1.7%; the plasma half-life period of 9 is approximately 98 min. The oral bioavailability of the other tested oseltamivir derivatives on guanidine-basis (9, 10) is not significantly different from derivative 6.

TABLE 8

Pharmacokinetic parameters of guanidine-based neuraminidase inhibitors

| Derivative | 9 | 9 | 6 | 10 |
|---|---|---|---|---|
| Administration | Iv | Oral | Oral | Oral |
| Rats (n) | 5 | 3 | 4 | 5 |
| MW [g/mol] | 326 | 326 | 370 | 468 (TFA) |
| Dose [mg/kg] | 10 | 50 | 50 | 50 |
| Dose (Equi) | 1 | 5 | 4.40 | 3.48 |
| AUC | 292.5 | 26.3 | 21.9 | 11.5 |
| $t_{max}$ [min] | — | 120.0 | 112.1 | 61.3 |
| $c_{max}$ [μg/ml] | — | 0.3 | 0.1 | 0.1 |
| MRT [min] | 54.1 | 129.2 | 205.7 | 124.8 |
| $t_{1/2}$ [min] | 120.0 | 186.3 | 97.7 | 50.0 |
| Bioavailability [%] | 100 | 1.8 | 1.7 | 1.1 |

The results of the intravenous administration of derivative 9 are shown in the following table and FIG. 9.

Average values of all plasma levels after intravenous administration of derivative 9

| Time | Conc. [μM] | Standard Deviation [μM] |
|---|---|---|
| 5 | 23.71 | 11.61 |
| 10 | 18.30 | 8.94 |
| 20 | 12.67 | 6.70 |
| 45 | 5.05 | 3.73 |

-continued

| Time | Conc. [μM] | Standard Deviation [μM] |
|---|---|---|
| 90 | 1.67 | 1.30 |
| 150 | 0.54 | 0.36 |
| 240 | 0.23 | 0.16 |
| 360 | 0.11 | 0.06 |

The oral administration of derivative 9 leads to the following plasma levels refer also to FIG. 10

Average values of all plasma levels of derivative 9 after oral administration of derivative 9

| Time [min] | Conc. [μM] | Standard Deviation [μM] |
|---|---|---|
| 0 | 0.00 | 0.00 |
| 30 | 0.22 | 0.06 |
| 60 | 0.19 | 0.07 |
| 90 | 0.24 | 0.08 |
| 120 | 0.91 | 0.78 |
| 180 | 0.17 | 0.03 |
| 240 | 0.12 | 0.09 |
| 360 | 0.00 | 0.00 |

The oral administration of derivative 6 leads to the following plasma levels refer also to FIG. 11

Average values of all plasma levels of derivative 9 after oral administration of derivative 6

| Time [min] | Conc. [μM] | Standard Deviation [μM] |
|---|---|---|
| 0 | 0.00 | 0.00 |
| 30 | 0.20 | 0.04 |
| 60 | 0.22 | 0.06 |
| 90 | 0.18 | 0.04 |
| 120 | 0.19 | 0.08 |
| 180 | 0.21 | 0.03 |
| 240 | 0.18 | 0.11 |
| 360 | 0.05 | 0.04 |

After oral administration of derivative 6, derivative 12 is detected as a metabolite. This can also be deduced from FIG. 12.

Average values of all plasma levels of intermediary metabolite 12 after oral administration of derivative 6

| Time [min] | Conc. [μM] | Standard Deviation [μM] |
|---|---|---|
| 0 | 0.00 | 0.00 |
| 30 | 0.20 | 0.07 |
| 60 | 0.16 | 0.10 |
| 90 | 0.20 | 0.06 |
| 120 | 0.19 | 0.07 |
| 180 | 0.08 | 0.05 |
| 240 | 0.01 | 0.03 |
| 360 | 0.00 | 0.00 |

FIG. 13 shows an overview of the results of the administration of guanidine-based inhibitors of neuraminidase (6, 9, 10).

MATERIAL AND METHODS: EMBODIMENTS

Syntheses (3R,4R,5S)-4-acetamido-5-(N-acetimidamido)-3-(1-ethylpropoxy)cyclohex-1-en-1-carboxylic acid ethyl ester hydrobromide (2)

1 g of oseltamivir (3.2 mmol) is dissolved in 10 ml of ethanol and the mixture is cooled to 0° C. 1.04 g of S-(naphthylmethyl)acetimidobromid (1.1 equivalents) are added to this solution and then stirred for one hour at room temperature. The mixture is concentrated subsequently in vacuo and taken up in about 80 ml water. This solution is washed with a little diethyl ether and concentrated in vacuo. The product (85%) contains at this point still small amounts of the parent compound, which could be removed by column chromatography (DCM/MeOH, 5-10%) only. Yield: 960 mg (71%) of a white solid.

DC: $R_f$=0.65 (DCM/MeOH, 9:1)

$^1$H-NMR (DMSO-$d_6$, 300 MHz): δ/ppm=0.79 (t, $^3J$=7.4 Hz, 3H), 0.85 (t, $^3J$=7.4 Hz, 3H), 1.23 (t, $^3J$=7.1 Hz, 3H), 1.44 ($m_c$, 4H), 1.83 (s, 3H), 2.11 (s, 3H), 2.33 ($m_c$, 1H), 2.67 (dd, $^2J$=17.6 Hz, $^3J$=4.7 Hz, 1H), 3.42 (quin, $^3J$=5.6 Hz, 1H), 3.82 ($m_c$, 1H), 4.05 ($m_c$, 1H), 4.17 (q, $^3J$=7.1 Hz, 2H), 4.35, ($m_c$, 1H), 6.69 ($m_c$, 1H), 8.04 (br d, $^3J$=9.0 Hz, 1H), 8.63 (br s, 1H), 9.25, 9.35 (2×br s, 1H).

MS (ESI): m/z=354 $[M+H]^+$ 3R,4R,5S)-4-acetamido-5-(N-acetimidamido)-3-(1-ethylpropoxy)cyclohex-1-en-1-carboxylic acid (3)

The amidine ethyl ester of oseltamivir (217 mg, 0.5 mmol) in 10 ml of MeOH is mixed with 1.5 ml of a 1 M methanolic KOH (3 equivalents) and stirred for 1 hour at 40° C. until no starting material is longer detectable on the DC. The solution is diluted with water and the pH value is adjusted with 1 M HCl to 7-8. The solution is concentrated to dryness then, and the residue is purified by flash chromatography on reverse phase (RP-18 column, eluent: water, detection: iodine chamber) purified. After lyophilization, the product is isolated as white powder.

Yield: 88% of a fine white powder.

$^1$H-NMR ($D_2O$, 300 MHz):

δ/ppm=0.84 (t, $^3J$=7.4 Hz, 3H), 0.89 (t, $^3J$=7.4 Hz), 3H, 1.38-1.63 (m, 4H), 2.03 (s, 3H), 2.23 (s, 3H), 2.43 ($m_c$, 1H), 2.82 (dd, $^2J$=17.5 Hz, $^3J$=4.8 Hz, 1H,), 3.53 (quin, $^3J$=5.4 Hz, 1H), 3.93-4.09 (m, 2H), 4.36 $m_c$, 1H), 6.71 (br s, 1H).

MS (ESI): m/z=348 $[M+Na]^+$, 326 $[M+H]^+$.

HRMS (ESI): m/z calcd. for $C_{16}H_{27}N_3O_4$ $[M+H]^+$: 326.20743. found: 326.20737.

(3R,4R,5S)-4-acetamido-5-[N—(N'-hydroxy)acetimidamido]-3-(1-ethylpropoxy)cyclohex-1-en-1-carboxylic acid ethyl ester (4)

465 mg of oseltamivir (1.49 mmol), 290 mg of DIPEA (389 μl, 1.5 equiv) are dissolved in 5 ml of dichloromethane, and cooled to 0° C. Freshly prepared acethydroximoyl chloride (209 mg, 1.5 equiv) is added slowly (dropwise) to this solution. The mixture is stirred for four hours at room temperature, mixed with 15 ml of water, stirred for an additional hour and then separated in a separating funnel. In order to increase the yield of the desired amidoxime, the aqueous phase is extracted four times with dichloromethane. The combined organic phases are dried over $Na_2SO_4$ and concentrated in vacuo. The crude product is purified by column chromatography on silica gel (DCM/MeOH, 9:1).

Yield: 70% of colorless, crystalline solid
DC: $R_f$=0.29 (DCM/MeOH, 9:1)
$^1$H-NMR (DMSO-$d_6$, 300 MHz):
δ/ppm=0.80 (t, $^3J$=7.4 Hz, 3H), 0.85 (t, $^3J$=7.4 Hz, 3H), 1.23 (t, $^3J$=7.1 Hz, 3H), 1.43 ($m_c$, 4H), 1.80 (s, 3H), 1.95 (s, 3H), 2.38 ($m_c$, 1H), 2.62 (dd, $^2J$=17.4 Hz, $^3J$=5.0 Hz, 1H), 3.40 (quin, $^3J$=5.6 Hz, 1H), 3.65 ($m_c$, 1H) 3.78 (dd, $^2J$=17.4 Hz, $^3J$=8.7 Hz, 1H), 4.15 (q, $^3J$=7.1 Hz, 2H), 4.19 ($m_c$, 1H), 6.67, ($m_c$, 1H), 6.81 (br d, 1H, $^3J$=9.1 Hz), 7.99 (d, 1H, $^3J$=8.6 Hz), 9.73 (br s, 1H).
MS (ESI): m/z=392 [M+Na]$^+$, 370 [M+H]$^+$, 354 [M–OH+H]$^+$.
HRMS (ESI): m/z calcd. for $C_{18}H_{31}N_3O_5$ [M+H]$^+$: 370.23365. found: 370.23379.

(3R,4R,5S)-4-acetamido-[N—(N' hydroxy)guanidino]-3-(1-ethylpropoxy)cyclohex-1-en-1-carboxylic acid ethyl ester (6)

213 mg of cyanamide (0.6 mmol) are dissolved in 5 ml of dry dioxane and exactly one equivalent of free hydroxylamine (20 mg) is added. It is stirred for 30 minutes at room temperature, concentrated and, after several fold addition and removal of dichloromethane and diethyl ether, a white solid is obtained.

Yield: 222 mg (100%) of a white solid
DC: $R_f$=0.20 (EtOAc/MeOH, 6:4)
$^1$H-NMR (DMSO-$d_6$, 300 MHz):
δ/ppm=0.80 (t, $^3J$=7.3 Hz, 3H), 0.84 (t, $^3J$=7.4 Hz, 3H), 1.24 (t, $^3J$=7.1 Hz, 3H), 1.40 (m, 4H), 1.83 (s, 3H), 1.99-2.07 (m, 1H), 2.86 (dd, $^2J$=16.7 Hz, $^3J$=2.5 Hz, 1H), 3.38 (quin, $^3J$=5.5 Hz, 1H), 3.49 (m, 1H), 3.80 (m, 1H), 4.01, (m, 1H), 4.14 (q, $^3J$=7.1 Hz, 2H), 4.24 (m, 1H), 4.92 (s, 2H), 6.64 (m, 1H), 7.72 (br s, 1H), 7.79 (d, $^3J$=8.8 Hz, 1H).
MS (ESI):
m/z=741 [2M+H]$^+$, 393 [M+Na]$^+$, 386, 371 [M+H]$^+$.
HRMS (ESI): m/z calcd. for $C_{17}H_{30}N_4O_5$ [M+H]$^+$: 371.22890. found: 371.22911.

(3R,4R,5S)-4-acetamido-5-[N—(N'-n-hexyloxycarbonyl)thioureido]-3-(1-ethylpropoxy)-cyclohex-1-en-1-carboxylic acid ethyl ester (7)

500 mg of oseltamivir (1.6 mmol) are dissolved in 50 ml of dry dichloromethane and equimolar amounts of hexyloxycarbonyl isothiocyanate (from an approximately 0.5 M solution in dichloromethane) are slowly added dropwise. After stirring for 2 hours at room temperature it is washed with 1% HCl, water, NaCl solution. The organic phase is dried over $Na_2SO_4$ and concentrated on a rotary evaporator. The crude product can be triturated or washed with cyclohexane and is sufficiently pure for the next reaction by this. For elemental analysis, the compound was further purified by silica gel column chromatography (Cy/EtOAc, 6:4).

Yield: 600 mg (75%) of a white-yellowish solid
DC: $R_f$=0.20 (Cy/EtOAc, 6:4)
$^1$H-NMR (DMSO-d6, 300 MHz):
δ/ppm=0.79 (t, $^3J$=7.4 Hz, 3H), 0.84 (t, $^3J$=7.3 Hz, 3H), 0.87 (t, $^3J$=6.8 Hz, 3H), 1.23 (t, $^3J$=7.2 Hz, 3H), 1.30 ($m_c$, 6H), 1.45 ($m_c$, 4H), 1.57 ($m_c$, 2H) 1.80 (s, 3H), 2.30 (dd, 1H, $^2J$=17.8 Hz, $^3J$=6.8 Hz), 2.90 (dd, 1H, $^2J$=17.8 Hz, $^3J$=5.0 Hz), 3.43 (quin, 1H, $^3J$=5.4 Hz), 4.07 ($m_c$, 4H), 4.16 (q, 2H, $^3J$=7.1 Hz), 4.55 ($m_c$, 1H), 6.74 (br s, 1H), 7.91 (br d, 1H, $^3J$=8.0 Hz), 9.98 (d, 1H, $^3J$=7.6 Hz), 10.90 (s, 1H).
MS (ESI):
m/z=500 [M+H]$^+$, 483, 412

(3R,4R,5S)-4-acetamido-5-[N—(N'-n-hexyloxycarbonyl)-(N''-(2-methoxypropane-2-yl)oxy) guanidino]-3-(1-ethylpropoxy)cyclohex-1-en-1-carboxylic acid ethyl ester (8)

358 mg of oseltamivir hexylthiourea (0.72 mmol) are dissolved in 10 ml of dry dichloromethane and 151 mg of O-(2-Methoxypropan-2-yl)hydroxylamine (2 equivalents), 251 μl DIPEA (2 equivalents), 276 mg of EDCI (2 equivalents) are added. The mixture is stirred for 1.5 days at room temperature, concentrated and worked up by column chromatography over silica gel (DCM/MeOH, 0-2%).

DC: $R_f$=0.39 (DCM/MeOH, 98:2)
Yield: 374 mg (91%) of a white solid, which is stored at −20° C.
$^1$H-NMR (DMSO-$d_6$, 300 MHz):
δ/ppm=0.83 ($m_c$, 9H) 1.27 ($m_c$, 12H), 1.27 ($m_c$, 12H), 1.45 ($m_c$, 4H), 1.57 ($m_c$, 2H), 1.80 (s, 3H), 2.30 (dd, 1H, $^2J$=18.1 Hz, $^3J$=7.1 Hz), 2.90 (dd, 1H, $^2J$=18.1 Hz, $^3J$=5.2 Hz), 3.06 (s, 3H), 3.43 (quin, 1H, $^3J$=5.6 Hz), 4.06 ($m_c$, 4H), 4.16 (q, 2H, $^3J$=7.1 Hz), 4.55 ($m_c$, 1H), 6.74 (s, 1H), 7.91 (d, 1H, $^3J$=8.1 Hz), 9.98 (d, 1H, $^3J$=7.8 Hz), 10.90 (s, 1H).
HRMS (ESI): m/z calcd. for $C_{28}H_{50}N_4O_8$ [M+H]$^+$: 571.37014. found: 571.37034.

(3R,4R,5S)-4-acetamido-5-(N-guanidino)-3-(1-ethylpropoxy)cyclohex-1-en-1-carboxylic acid (9)

a) Pharmacokinetic Characterization of the Inhibitors and Prodrugs

1. Stability Studies for the Amidine Effective Form (3) and Prodrugs Thereof (2, 4) as Well as and the Guanidine Effective Form (9) and Prodrugs Thereof (6, 10) Over 6 h The stability tests were carried out in 50 mM potassium phosphate buffer at a concentration of 0.2 mM. For this purpose, a 2 mM stock solution was prepared in 10 mM potassium phosphate buffer pH 7.4 and diluted 1:10 with phosphate buffer of respective pH value. Each compound was tested at pH 2.0, 7.4 and 9.0. For this purpose, every 30 min a sample was analyzed by HPLC and the stability was tested over 6 h. The concentration at t=0 min was set as 100%.

In addition, the substances were tested in human and murine plasma. Therefor, 630 μl of the plasma as mixed with 70 μl of a 2 mM stock solution of each compound in 10 mM phosphate buffer pH 7.4. The incubations were performed in a shaking water bath at 37° C. The incubation was terminated at the times 15, 30, 45, 60, 90 and 120 min by removal of 100 μl sample and addition of 100 μl acetonitrile. The samples were centrifuged (12,000 rpm/10 min) and the supernatant surveyed by HPLC.

The stability studies were analyzed using the following HPLC method.

HPLC Method

| HPLC-System | Waters Autosampler 717plus, Waters 600 Controller, Waters 600 Pump, Waters 2487 Dual λ Absorbance Detector and EZChrom Elite Client/Server recording and analysis software (version 2.8.3) |
|---|---|
| Column: | LiChrospher 60 RP-select B (125 × 4 mm, 5 μm) with a RP-select B guard column (4 × 4 mm). |
| Flow: | 1 ml/min |
| Eluant: | for 3, 9    60% 10 mM $KH_2PO_4$/0.1% TFA pH 3.0<br>40% MeOH |

| | for 2, 4, 6, 10 | 50% 10 mM KH₂PO₄/0.1% TFA pH 3.0 50% MeOH |
|---|---|---|
| Running time: | 7.5 min | |
| Detection: | 230 nm | |
| Injection volume: | 10 µl | |
| Retention times: | 4 | 4.2 ± 0.1 min |
| | 9 | 4.4 ± 0.2 min |
| | 3 | 4.5 ± 0.2 min |
| | 6 | 4.6 ± 0.1 min |
| | 2 | 4.8 ± 0.1 min |
| | 10 | 3.7 ± 0.1 min |

Stability Studies for the Amidine Effective Form (3) and Guanidine Effective Form (9) Over 2 Weeks
Studies at pH 7.4:

The storage stability in dissolved form was determined at a concentration of 0.2 mg/ml. For this purpose, the compound was dissolved in 50 mM KH₂PO₄ buffer pH 7.4 or in aqua bidest and stored for the investigation period at RT (pH 7.4) or in a refrigerator at 4° C. (pH 7.4 or aqua bidest). The concentration of the effective form was determined by HPLC after 12 h, 1 d, 2 d, 4 d, 7 d and 14 d.

2. Solubility Assays of the Compounds Tested
Determining the Solubility at Different pH Values:

The solubility of the compounds was determined in phosphate buffer at different pH values (2.0, 7.4 and 9.0). Therefor, a few mg of the compounds were weighed and mixed with the volume of 50 mM KH₂PO₄ buffer of respective pH value for a 50 mM solution. If the compound had not completely dissolved, the suspension was shaken for 30 min. Subsequently, the undissolved portion was removed by centrifugation at 10.000 rpm for 15 min, and the concentration in the supernatant was determined by HPLC.

3. Determination of Protein Binding of the Amidine Effective Form (3) as Well as of Prodrugs Thereof (2, 4) and of the Guanidine Effective Form (9) as Well as of Prodrugs Thereof (6, 10)

The plasma protein binding was carried out in three different concentrations (10, 25, and 50 µM). A 4% albumin solution was used as protein solutions. In each case, 50 µl of a 10-fold concentrated substance solution were pipetted in 450 µl of the protein solution. The incubation was carried out for 15 minutes in the shaking water bath at 37° C. Subsequently, the samples were transferred in ultra-filtration units (Vivaspin 500, 10 kDa cut-off) and centrifuged for 15 min at 10.000 rpm. The filtrate was analyzed by HPLC. In addition, a control was run for each concentration, which was not treated with protein and not centrifuged. Another control without protein supplement, however centrifuged through the filtration unit, showed that the prodrugs are not retained by the membrane and were used to validate the methodology.

In addition, the protein binding of the two effective forms of oseltamivir-amidine (3) and oseltamivir-guanidine was (9) examined in human plasma. Therefor, instead of the 4% albumin solution, human plasma was used. A protein binding of 3.7±1.4% for compound 3 and 8.6±3.0% for compound 9 was determined. As anticipated, the values are somewhat higher than the values obtained with the 4% albumin solution and are due to the presence of other plasma proteins (e.g., $\alpha_1$-acidic glycoprotein) besides the albumin.

4. Investigation of the Bioactivation of the Various Prodrugs (2, 4, 6, 10)
Determination of the Activation of the Prodrugs with Different Subcellular Enzyme Systems:

The activation of the prodrugs into their effective forms was determined in vitro by subcellular enzyme preparations. As enzyme preparations 9000G supernatants, microsomes and mitochondria from human and porcine liver tissues were used. The incubation mixtures were composed of 500 µM prodrug, 500 µM NADH, 1 U of esterase and 0.3 mg of enzyme preparation dissolved in 150 µl 100 mM phosphate buffer pH 6.3. The incubation was carried out for 30 min at 37° C. in the shaking water bath. By adding 150 µl acetonitrile, the incubation was terminated. Afterwards, the samples were shaken for 10 min and the precipitated protein removed by centrifugation at 10.000 rpm for 15 min. The supernatant was measured with the help of HPLC.

HPLC Method for the Determination of the Effective Forms (3/9) in Addition to the Prodrugs (2, 4/6, 10)

| HPLC system | Waters Alliance HPLC system with Waters e2695 XC separations module, Waters 2998 photodiode array detector and Empower 2 software | |
|---|---|---|
| Column: | LiChrospher 60 RP-select B (125 × 4 mm, 5 µm) with C18 guard column (4 × 4 mm) | |
| Flow: | 1 ml/min | |
| Mobile phase: | 70% | 10 mM KH₂PO₄/0.1% TFA pH 6.5 |
| | 30% | MeOH |
| Running time: | 12 min | |
| Detection: | 210 nm | |
| Injection volume: | 10 µl | |
| Retention time: | 3 | 4.8 ± 0.2 min |
| | 9 | 4.7 ± 0.2 min |
| | 10 | 24.8 ± 0.4 min |
| | 6 | 25.2 ± 0.3 min |
| | 4 | 26.6 ± 0.3 min |
| | 2 | 26.6 ± 0.3 min |

Antiviral Effectivity
Determination of the Antiviral Effectivity in the Chemiluminescence Based Neuraminidase (NA)—Inhibition Assay Following influenza viruses were used for the studies:
H1N1 viruses: A/Jena/5258/2009, A/Jena/5555/09, A/HH/1580/09, A/342/2009 (oseltamivir resistant)
H₂N₃ viruses: Hong Kong/8/68, Saxony/6/02, Berlin/10/04, Rhineland-Palatinate/3911/03.

The inhibition of viral neuraminidase by the test compounds 3 and 9 as well as by the control substances was checked using the commercially available NA-Star kit (Tropix, Applied Biosystems, Darmstadt).

According to the recommendations of the manufacturer, the optimal dilution of the test viruses for the subsequent inhibition assay was determined in a preliminary test first. For this, the virus suspensions were diluted in NA-Star buffer (dilution factor of 3) in the absence of neuraminidase inhibitors (NAI). The virus dilution leading to a signal and background ratio of 40:1 was subsequently used in the NA inhibition assays for determining the 50% inhibitory concentrations.

In NA-inhibition assay for the 6 virus controls per plate 25 µl assay buffer or 25 µl of the test (three parallels per dilution) or the control substance (two parallels per dilution) in assay buffer were applied into the individual wells of the microtiter plate with 96 wells. Then, 25 µl of a virus dilution was added to each well. After a 20 minute incubation time at 37° C., the substrate was diluted 1:500 in assay buffer and 10 µl was added to each well respectively. The measurement of chemiluminescence was performed 30 min later in a plate reader (microtiter plate luminometer, Dynex Technology). For the evaluation of the assays, the average of the measured chemiluminescence of the 6 untreated virus controls was taken as 100% value for the NA activity and used for the calculation of the relative NA-activity of the substance treated individual wells. From the obtained average dose-response curve of two independent assays, subsequently the 50% inhibitory concentration (IC50) of the test and control substances was calculated by linear interpolation in EXCEL.

Determination of the Antiviral Effectivity of the Test Substances in Virus Yield (VY)-Inhibition Assay Cells: MDCK cells Influenza viruses: a) A/Jena/5258/2009 (pandemic H1N1; oseltamivir-sensitive)

b) A/342/2009 (H1N1; oseltamivir-resistant)

By adding antiviral effective agents (100 µl/well; 3 parallels/concentration/test substance and two parallels/concentration/control substance, dilution factor of 10) virus replication can be selectively inhibited. This can be determined experimentally on the basis of reduced viral titer in the supernatant.

In the assay, 2 days old closed cellular monolayers were inoculated with a dose of virus, which leads 48 hours post infection to an incomplete cytopathic effect in the 3 untreated virus controls. After an incubation for one hour at 37° C., the virus which was not bound to the cells was removed by 3 consecutive washings of each well and 100 µl test medium (cell and virus controls) or of the substance dilutions was added. Following a 48 hour incubation at 37° C., the supernatants of each well were removed for the subsequent determination of the virus titer.

The determination of the virus titer was performed in 2 days old MDCK cell monolayers in microtiter plates. First, logarithmic dilution series (maximum dilution factor of 10; maximal dilution $10^{-7}$) were created from the supernatants from the VY inhibition assay for this purpose. These were inoculated on cells (4 wells/virus dilution respectively) and incubated for 4 days at 37° C. During this time the cytopathic effect was formed. After fixing and staining the cells with a crystal violet formalin solution, the visual evaluation was carried out on a light box.

Subsequently, the virus titers were calculated according to Reed and Muench. The average of the virus titers of the three virus controls was taken as 100% for the calculation of the titer reduction.

Determination of the Antiviral Effectivity of the Test Substances in cpE Inhibition Assay The replication of the viruses used in the assay leads through a strongly pronounced cytopathic effect (cpE) to a total destruction of the host cells. By adding antiviral effective substances (100 µl/well; 3 parallels/concentration, dilution factor of 2) the virus-induced cpE can be selectively inhibited. In the assay, untreated and substance-treated enclosed cell lawns were inoculated with a dose of virus that leads 48 h after infection to a complete cpE in the untreated virus controls. At this time, the remaining adherent cells were fixed and stained with a crystal violet/formalin solution. After dye elution, the inhibition of virus-induced cpE was quantified photometrically in a Dynatech plate reader.

Calculating the antiviral effect was carried out by comparing the optical densities of the substance-treated and untreated, virus infected cells with the average optical density of the cell controls, which was set as 100%. Based on the mean dose-response curve of 2 experiments, the dilution was calculated by linear interpolation in EXCEL, which prevented the formation of the virus-induced cpE by 50% (IC50).

Cytotoxicity Assay for Determination of the 50% Cytotoxic Dose ($CC_{50}$) of the Test Substances in MDCK (Madin Darby Canine Kidney) Cell Lawn MDCK cells were seeded in microtiter plates and incubated for 48 h in an incubator at 5% $CO_2$, 37° C. and 95% humidity to form a closed cell lawn. Thereafter, the medium was removed and the substances were applied in culture medium in various concentrations (100 µl/well, 3 parallels/concentration, dilution factor 2). For control value determination (six untreated cell controls) 100 µl medium were used respectively. 72 h after substance administration and incubation the staining of the cells is carried out with crystal violet/methanol. After the dissolution of the dye, the optical density (OD) of each well was measured in a plate photometer from Dynatech (550/630 nm) and compared with the average of the cell controls. The average of the controls was taken as 100%.

Animal Study

Operation/Preparation of Animals

Sprague Dawley (SD) rats were supplied for habitation 10 days before the start of the experiment, weighing ~300-350 g and kept in an air conditioned room with a constant temperature of 20° C. and a humidity of 50%. In this room there was a day-night rhythm of twelve hours. The dark phase began daily at 18 o'clock and turned over to the light phase at 6 clock. The rats were kept over the acclimatization period in standard cages of the size 3 (length: 42 cm, width 26 cm, height: 15 cm) and transferred three days before commencement of an experiment into a special experimental room, placed in the identical environmental conditions. They received a maintenance diet (maintenance diet for rats and mice; No. 1320; Altromin) and tap water ad libitum.

The animal experiments described herein were conducted according to the "NIH Guideline" and the corresponding policy on handling and use of experimental animals after approval by the Ministry of Agriculture, Environment and Rural Areas of Schleswig-Holstein.

A catheter was implanted in the vein as well as in the arteria femoralis of rats receiving an i.v. administration. Rats receiving only oral administration of substances received a venous catheter only.

The rats were anesthetized with pentobarbital (60 mg/kg i.p.) and were additionally narcotized with diethyl ether in case of insufficient depth of anesthesia. After shaving the neck area and the right inguinal region, the rats were placed on an electrical heating stage (EBERLE, type 52102) to maintain body temperature in the supine position and the hind legs were fixed. Along the groin an about 1.5 cm long incision was set. Subsequently, the vascular strand of the arteria femoralis, vena femoralis and nervus femoralis was set free by blunt preparation for a length of about 1 cm.

After separation of the vena femoralis, a cotton thread was placed proximally around it and the vessel was closed reversibly by tightening. Approx. 5 mm in distal direction the vessel has been ligated by means of a second thread, so as to create a congestion. With a vascular scissors, a small incision was carried out in the vessel in the area of the congestion (about ⅓ of the total congestion length from the distal ligature away) and polyethylene tube (length: 26 cm; ID: 0.58 mm, OD 0.96 mm) filled with a heparin solution (250 IU/ml) was introduced 3 cm towards proximal up to the vena cava by means of a container spreader. With the proximal and distal threads the catheter was fixed to the vessel.

The arteria femoralis was, in contrast to the vena femoralis, at first closed by a distal ligature and then impounded proximally by tightening the thread. Here, too, a catheter was implanted as described above. Due to the small inner diameter of the artery, a specially made artery catheter was used, consisting of a polyethylene tube (length: 26 cm, ID:

0.58 mm, OD 0.96 mm) and of a 3 cm long welded polyethylene tube (ID: 0.28 mm, OD: 0.61 mm).

After including the catheter, the animal was placed in the prone position and a 5 mm wide incision was placed in the neck. By means of a metal rod and a tube, the catheters, which were sealed with wire pins, were pulled from the ledge to the neck, fixed in the neck with cotton thread and cut to approximately 3 cm in length.

In the supine position again, the subcutaneous fat and then the epidermis were first sewn together with three to four double buttonhole stitches and disinfected with Betaisadonna® solution. On the following days the catheters were rinsed in the morning and the evening with 300 µl heparin solution (250 IU/ml) each. The operated rats were kept from the day of catheter insertion individually in experimental cages made of plexiglas with the dimensions height: 20 cm, width: 22 cm, and length: 25 cm or kept in standard cages of size 3.

The catheterized animals were kept after surgery for a day in the experimental room and individually in their experimental cages. The application of the test compounds was carried out on the second day after the operation. On the experimental day, the rats were weighed one hour prior to the test and the arterial catheter was flushed with 300 µl of heparin solution. Subsequently, the i.v. or oral administration of the compounds was carried out.

Implementation of the Animal Study

The oseltamivir derivative 3 was administered intravenously to 5 rats at a concentration of 10 mg/kg. Oral administration of the neuraminidase inhibitors (2, 4) has been carried out to 5 or 6 rats at a dosage of 50 mg/kg. In addition, derivative 3 was administered (50 mg/kg) to 3 rats orally. The oral administrations were performed as a suspension or solution made with gum arabic (10% w/v) by gavage.

The oseltamivir derivative 9 was administered intravenously to 5 rats at a concentration of 10 mg/kg. Oral administration of the neuraminidase inhibitor (6, 10) has been carried out at 4, or 5 rats at a dose of 50 mg/kg. Additionally, derivative 9 was administered (50 mg/kg) to 3 rats orally. The oral administrations were made as suspension or solution with gum arabic (10% w/v) by gavage.

After i.v. administration, plasma samples were taken at 5, 10, 20, 45, 90, 150, 240 and 360 min, respectively after oral administration after 30, 60, 90, 120, 180, 240 and 360 min. To this, in each case 300 µl of whole blood were taken using an insulin syringe and transferred into EDTA-coated Microvettes CB 300 (Sarstedt, Nümbrecht). After each withdrawal it was rinsed with 100 µl 0.9% saline or every 60 min with heparin solution (250 IU/ml). The blood sample was shaken briefly and put until centrifugation (4° C.; 14000 U/min; 10 min) on ice. Subsequently, the samples were frozen at −80° C.

The killing was carried out by decapitation 6 h after drug administration with a guillotine. In the following, the organs were removed. All organs were cleaned and frozen in dry ice cooled 2-methyl butane. Liver, kidney, and lung were harvested.

Analysis of Plasma Samples

The plasma samples were processed and analyzed by HPLC. Therefor, the plasma samples were thawed at room temperature. In each case, 80 µl methanol (+0.2% TFA) were prepared and subsequently 80 µl of the plasma samples were pipetted into. The samples were shaken for 45 min to precipitate plasma proteins. The samples were frozen at −80° C., thawed and shaken for another 15 min. The samples were centrifuged for 15 min at 13.000 RPM and the supernatant was transferred into HPLC vials. In each case 50 µl were used for the determinations by LC/MS.

The animal studies were evaluated using the following LC/MS method.

LC/MS Method

| HPLC System: | Agilent 1100 binary pump, Agilent 1100 diode array detector, Agilent 1100 well-plate autosampler, Degasser G1322A |
|---|---|
| Column: | LiChrospher 60 RP-select B (125 × 3 mm, 5 µl) with a RP-select; B guard column (4 × 4 mm) |
| Mass spectrometer | Esquire-LC |
| Interface: | ESI (electron impact ionization) |
| Nebulizer: | 40.0 psi |
| Dry gas: | 8.0 ml/min |
| Dry temperature: | 350° C. |
| HV capillary | 5000 V |
| Mobile phase: | A 0.1% TFA in aqua bidest (pH 2.5) B 0.1% TFA in MeOH |

| Gradient profiles: | time | A [%] | B [%] |
|---|---|---|---|
| | 0 | 55 | 45 |
| | 8 | 25 | 75 |
| | 10 | 25 | 75 |
| | 11 | 55 | 45 |
| | 17 | 55 | 45 |

| Flow rate: | 0.3 ml/min |
|---|---|
| Running time: | 17 min |
| Detection: | PDA (190-400 nm) |
| Injektion volume: | 50 µl |
| Retention times: | 3   5.1 ± 0.3 min |
| | 9   5.1 ± 0.3 min |
| | 11   5.2 ± 0.3 min |
| | 12   5.2 ± 0.3 min |

LITERATURE

Figure 1:
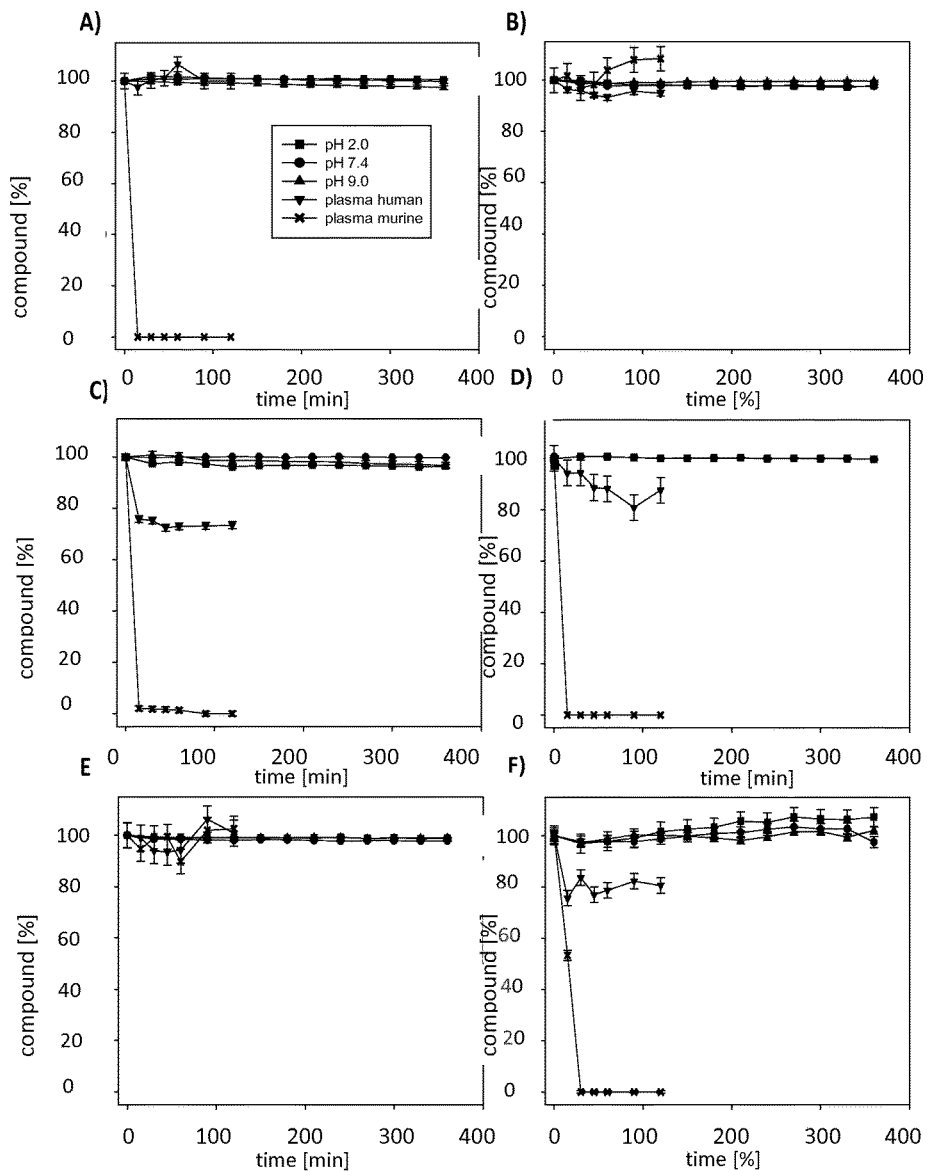
FIG. 1: Stability of some compounds of the invention at different pH values in murine or human plasma
Figure 2:
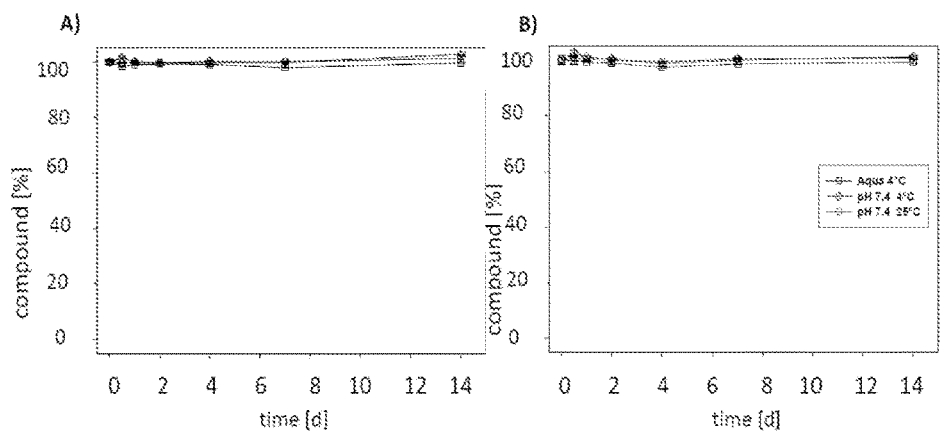
FIG. 2: Stability of the active forms of A) 3 and B) 9 in different media and with different temperatures
Figure 3:
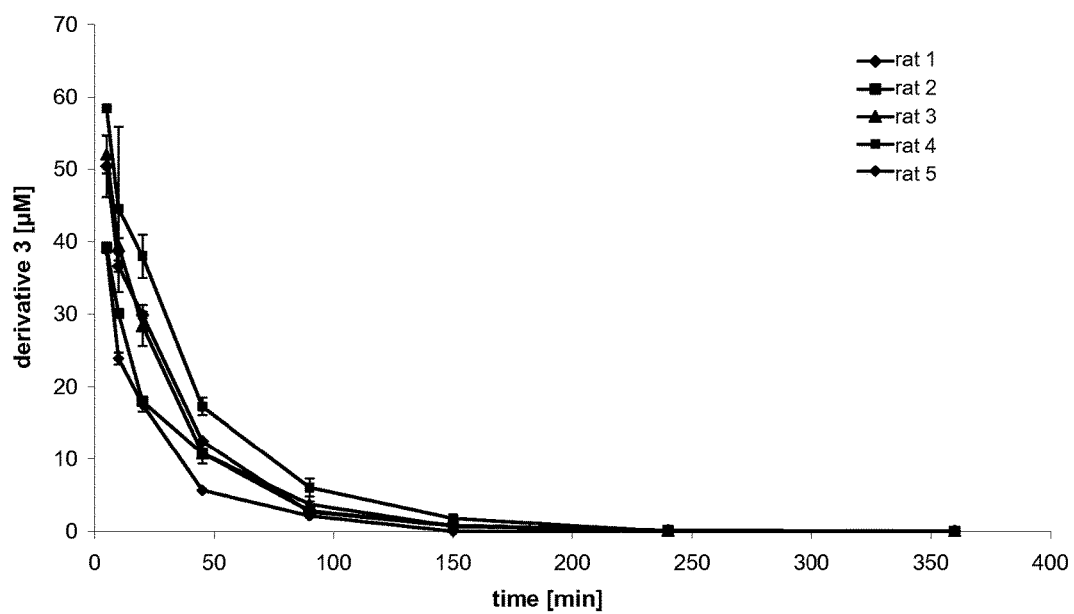
FIG. 3: Plasma levels of derivative 3 after intravenous administration of derivative 3 into 5 rats in total
Figure 4:
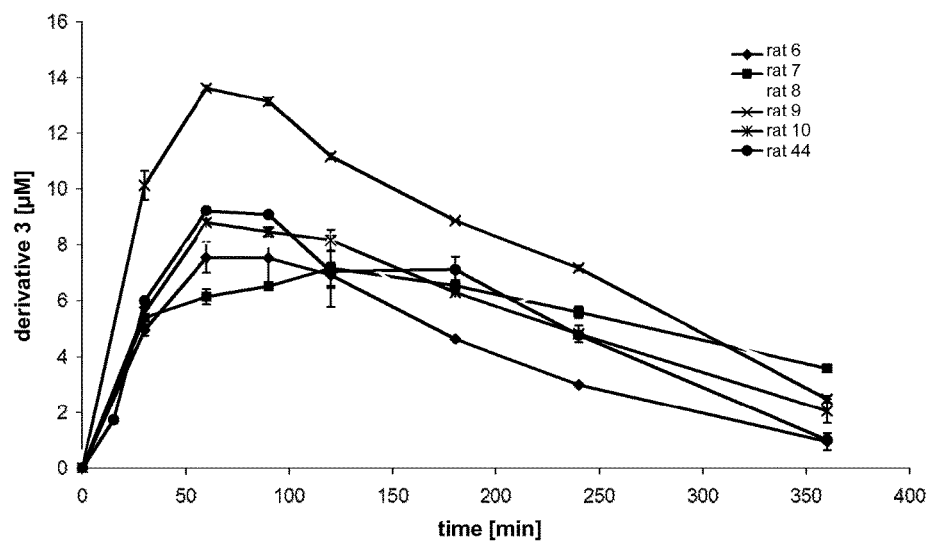
FIG. 4: Plasma levels of derivative 3 after oral administration of derivative 4
Figure 5:
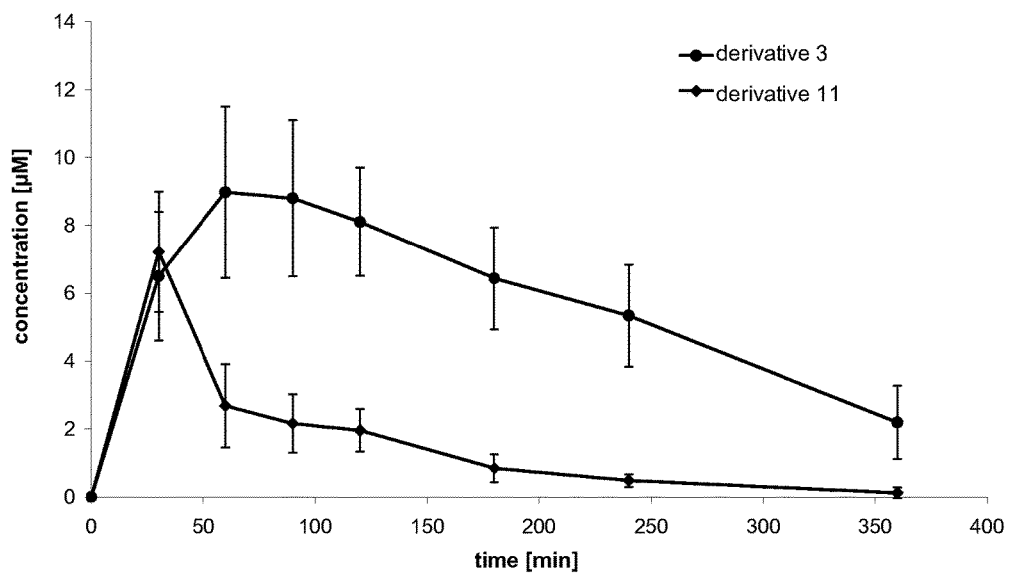
FIG. 5: Plasma levels of derivative 3 and metabolite 11 after oral administration of derivative 4
Figure 6:
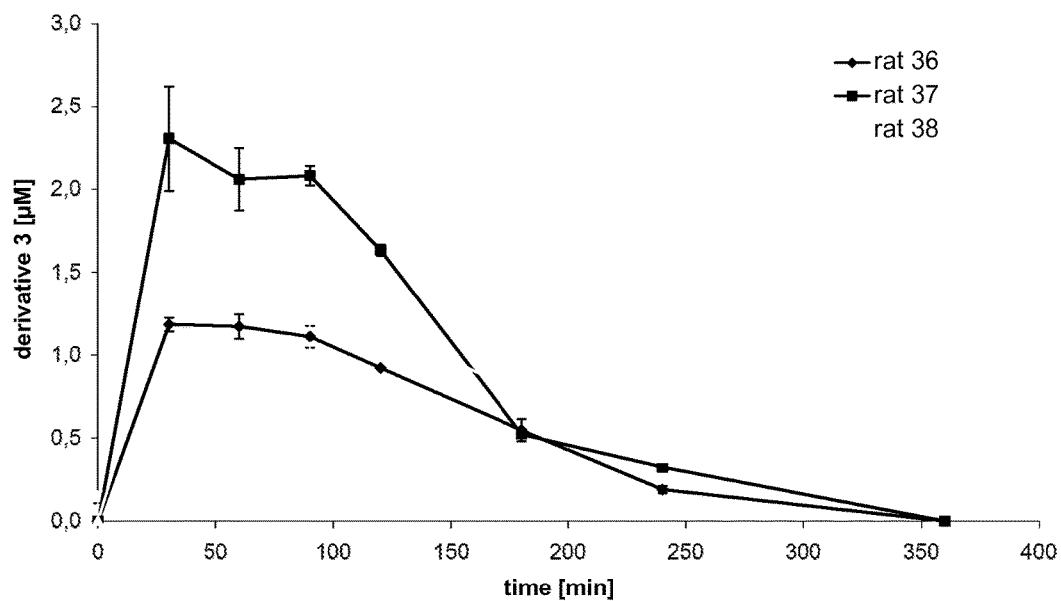
FIG. 6: Plasma levels of derivative 3 after oral administration of derivative 3
Figure 7:
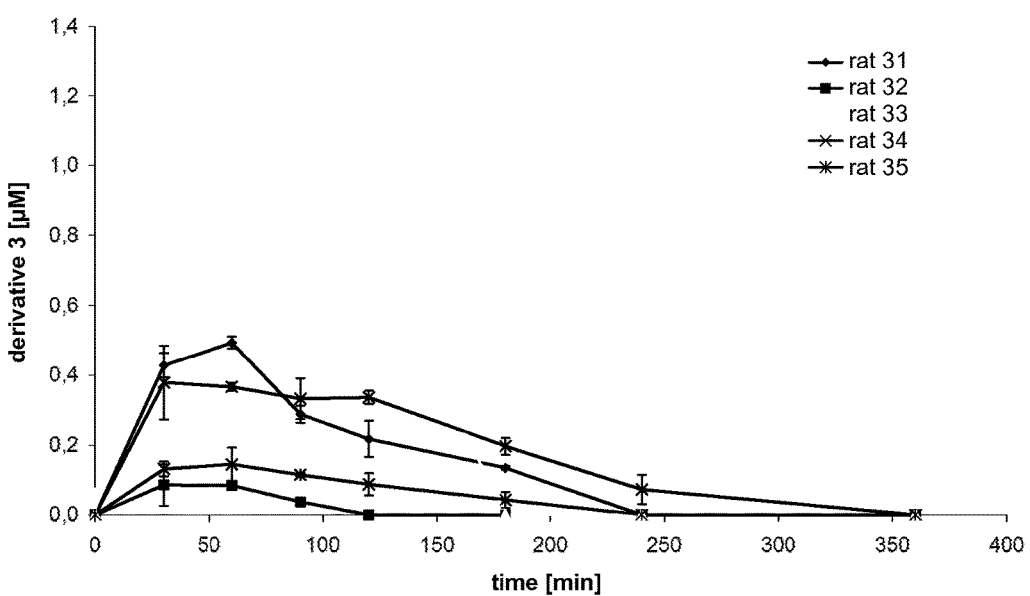
FIG. 7: Plasma levels of derivative 3 after oral administration of derivative 2
Figure 8:
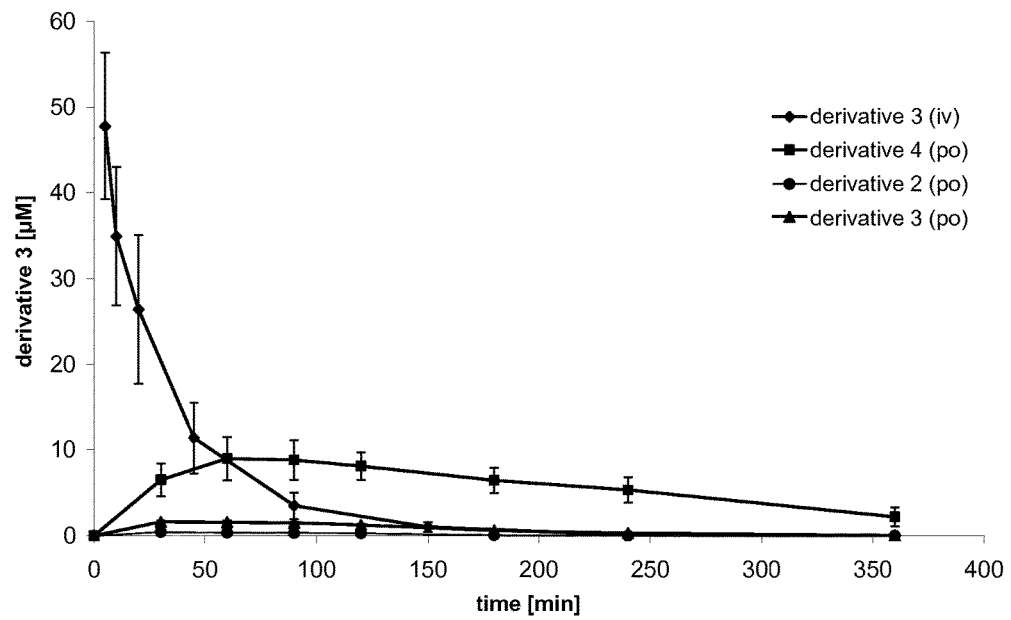
FIG. 8: Plasma levels of derivative 3 after administration of amidine based neuramidase inhibitors
Figure 9:
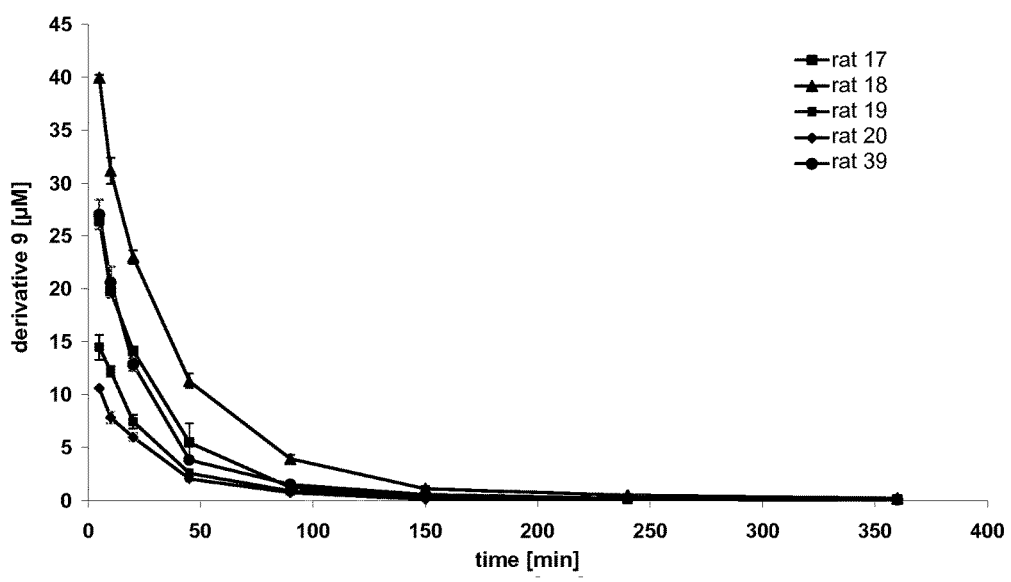
FIG. 9: Plasma levels of derivative 9 after i.v. administration of derivative 9
Figure 10:
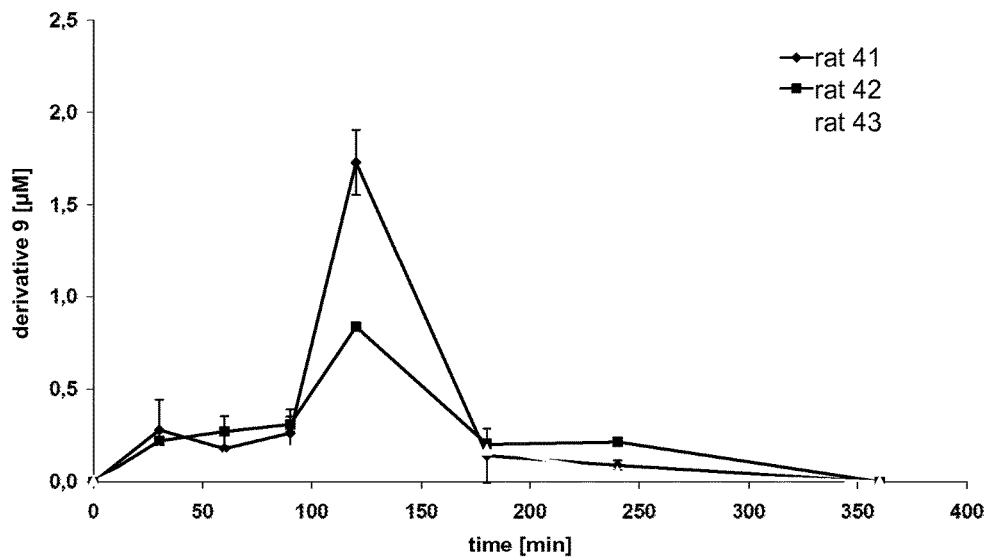
FIG. 10: Plasma levels of derivative 9 after oral administration of derivative 9
Figure 11:
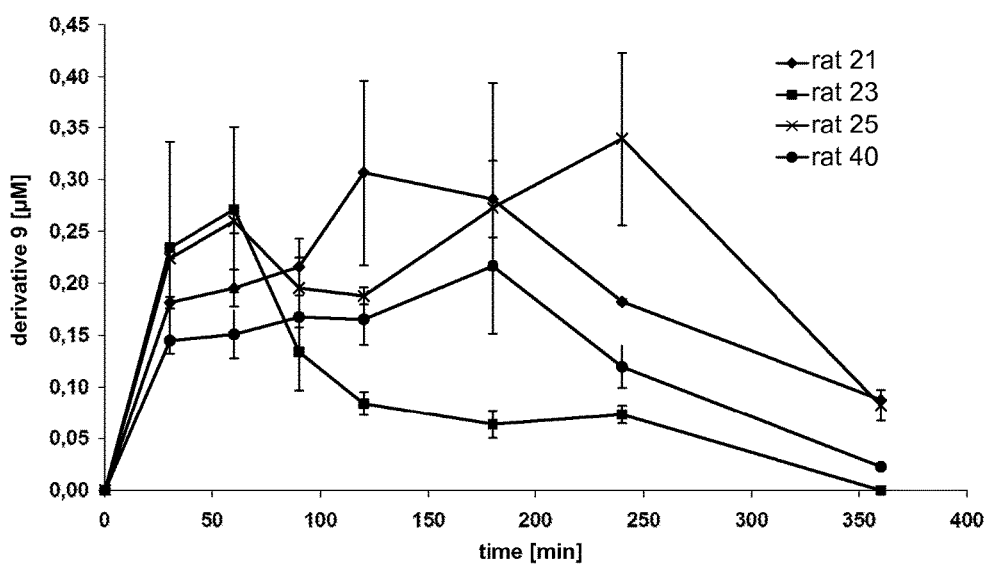
FIG. 11: Plasma levels of derivative 9 after oral administration of derivative 6
Figure 12:
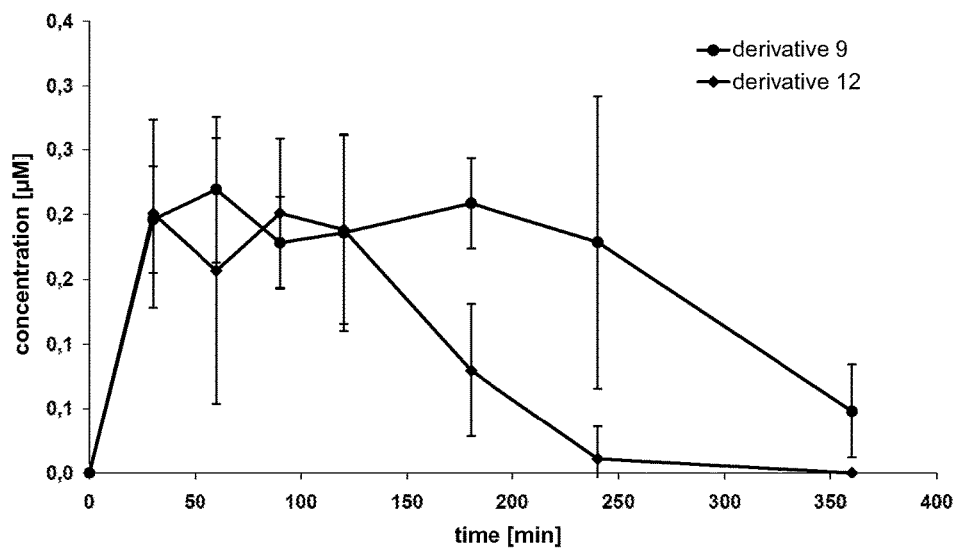
FIG. 12: Plasma levels of derivative 9 and metabolite 12 after oral administration of derivative 6
Figure 13:
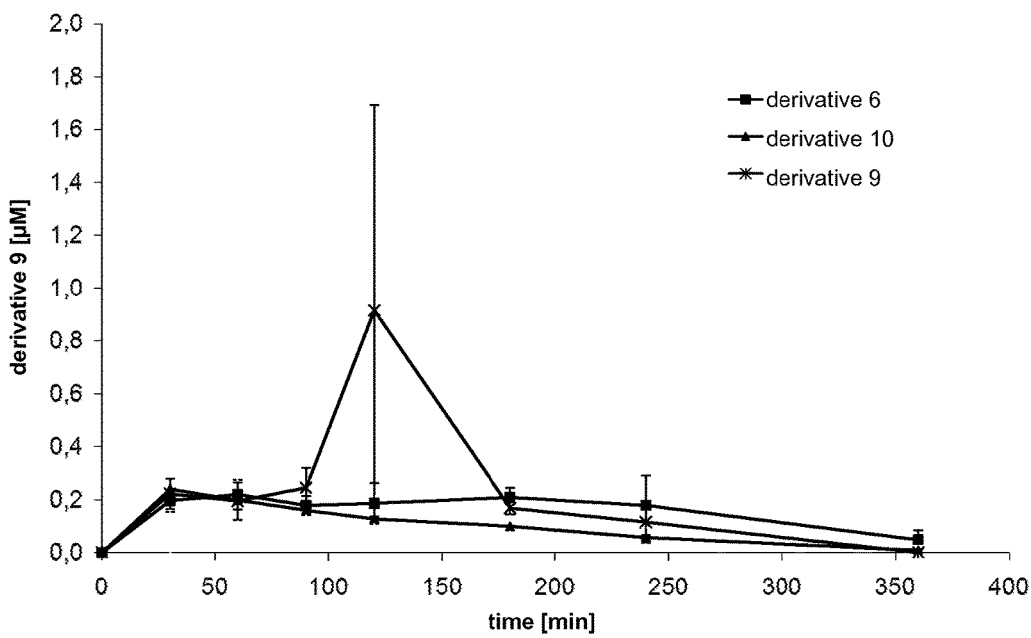
FIG. 13: Plasma levels of derivative 9 after application of the guanidine based neuramidase inhibitors

1. Hanessian, S.; Wang, J.; Montgomery, D.; Stoll, V.; Stewart, K. D.; Kati, W.; Maring, C.; Kempf, D.; Hutchins, C.; Layer, W. G. Design, synthesis, and neuraminidase inhibitory activity of GS-4071 analogues that utilize a novel hydrophobic paradigm. *Bioorg Med Chem Lett* 2002, 12, 3425-9.

2. Du, Q. S.; Wang, S. Q.; Chou, K. C. Analogue inhibitors by modifying oseltamivir based on the crystal neuraminidase structure for treating drug-resistant H5N1 virus. *Biochem Biophys Res Commun* 2007, 362, 525-31.

3. Masuda, T.; Shibuya, S.; Arai, M.; Yoshida, S.; Tomozawa, T.; Ohno, A.; Yamashita, M.; Honda, T. Synthesis and anti-influenza evaluation of orally active bicyclic ether derivatives related to zanamivir. *Bioorg Med Chem Lett* 2003, 13, 669-73.

4. Li, Y.; Zhou, B.; Wang, R. Rational design of Tamiflu derivatives targeting at the open conformation of neuraminidase subtype 1. *J Mol Graph Model* 2009, 28, 203-19.

5. D'Souza, C.; Kanyalkar, M.; Joshi, M.; Coutinho, E.; Srivastava, S. Search for novel neuraminidase inhibitors: Design, synthesis and interaction of oseltamivir derivatives with model membrane using docking, NMR and DSC methods. *Biochim Biophys Acta* 2009, 1788, 1740-51.

6. Wang, S. Q.; Cheng, X. C.; Dong, W. L.; Wang, R. L.; Chou, K. C. Three new powerful oseltamivir derivatives for inhibiting the neuraminidase of influenza virus. *Biochem Biophys Res Commun* 401, 188-91.

7. Carbain, B.; Collins, P. J.; Callum, L.; Martin, S. R.; Hay, A. J.; McCauley, J.; Streicher, H. Efficient synthesis of highly active phospha-isosteres of the influenza neuraminidase inhibitor oseltamivir. *ChemMedChem* 2009, 4, 335-7.

8. Shie, J. J.; Fang, J. M.; Wang, S. Y.; Tsai, K. C.; Cheng, Y. S.; Yang, A. S.; Hsiao, S. C.; Su, C. Y.; Wong, C. H. Synthesis of tamiflu and its phosphonate congeners possessing potent anti-influenza activity. *J Am Chem Soc* 2007, 129, 11892-3.

9. Smee, D. F.; Huffman, J. H.; Morrison, A. C.; Barnard, D. L.; Sidwell, R. W. Cyclopentane neuraminidase inhibitors with potent in vitro anti-influenza virus activities. *Antimicrob Agents Chemother* 2001, 45, 743-8.

10. Zhang, J.; Wang, Q.; Fang, H.; Xu, W.; Liu, A.; Du, G. Design, synthesis, inhibitory activity, and SAR studies of hydrophobic p-aminosalicylic acid derivatives as neuraminidase inhibitors. *Bioorg Med Chem* 2008, 16, 3839-47.

11. Albohy, A.; Mohan, S.; Zheng, R. B.; Pinto, B. M.; Cairo, C. W. Inhibitor selectivity of a new class of oseltamivir analogs against viral neuraminidase over human neuraminidase enzymes. *Bioorg Med Chem* 19, 2817-22.

The invention claimed is:

1. A compound, wherein the compound is amidoxime (3R,4R,5S)-4-Acetamido-5-[N—(N'-hydroxy)acetimidamido]-3-(1-ethylpropoxy) cyclohex-1-en-1-carboxylic acid ethyl ester having the chemical structure:

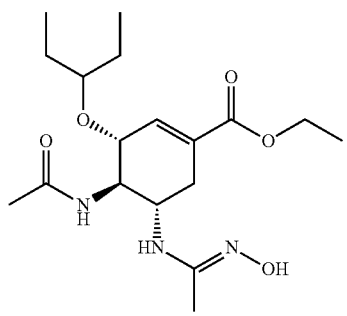 [SMILES: CCOC(=O)C1=C[C@@H](OC(CC)CC)[C@H](NC(C)=O)[C@@H](N/C(C)=N/O)C1]

or (3R,4R,5S)-4-acetamido-5-(N-acetimidamido)-3-(1-ethylpropoxy)cyclohex-1-en-1-carboxylic acid having the chemical structure:

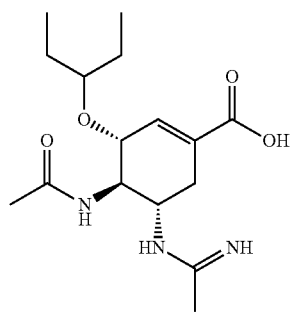 [SMILES: CCC(CC)O[C@@H]1C=C(C(=O)O)C[C@H](NC(C)=N)[C@H]1NC(C)=O]

and/or pharmaceutically acceptable salts, solvates, R/S enantiomers and/or prodrugs thereof.

2. A composition containing a compound according to claim 1 formulated for administration to a mammal.

3. An influenza neuraminidase inhibitor, wherein the inhibitor is amidoxime (3R,4R,5S)-4-acetamido-5-[N—(N'-hydroxy) acetimidamido]-3-(1-ethylpropoxy)cyclohex-1-en-1-carboxylic acid ethyl ester having the chemical structure:

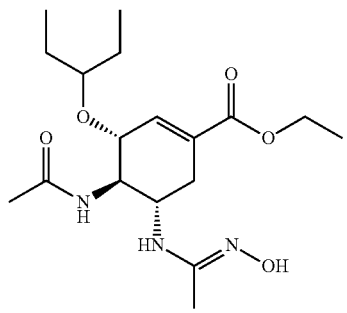 [SMILES: CCOC(=O)C1=C[C@@H](OC(CC)CC)[C@H](NC(C)=O)[C@@H](N/C(C)=N/O)C1]

or (3R,4R,5S)-4-acetamido-5-(N-acetimidamido)-3-(1-ethylpropoxy)cyclohex-1-en-1-carboxylic acid having the chemical structure:

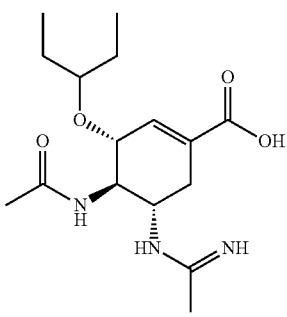 [SMILES: CCC(CC)O[C@@H]1C=C(C(=O)O)C[C@H](NC(C)=N)[C@H]1NC(C)=O]

as well as pharmaceutically acceptable salts, solvates or prodrugs thereof.

4. A method for preparing a compound according to the general structural formula

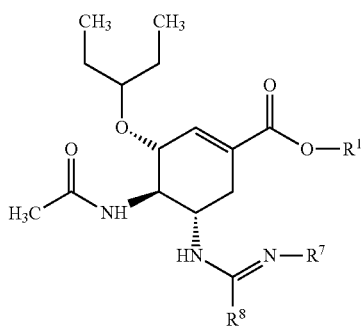

as well as the pharmaceutically acceptable salts, solvates, R/S enantiomers and/or prodrugs thereof, wherein
$R^1$ is H, or a branched or unbranched, saturated or unsaturated, substituted or unsubstituted hydrocarbon chain having a chain length of 1 to 12,
$R^7$ is H or OH,
$R^8$ is H, $R^9$, $NH_2$, $NHR^9$, $N(R^9)_2$ or $NHCOOR^1$,
$R^9$ is a branched or unbranched, substituted or unsubstituted alkyl having a chain length of 1 to 4 carbon atoms and
wherein substituents for $R^1$ and $R^9$ are selected from the group consisting of fluorine, chlorine, bromine, iodine, oxygen, sulfur, alkoxy, acyloxy, hydroxyl, mercapto, cyano, nitro, or thio alkoxy group, and a functionality which is blocked with a protecting group, comprising reacting an oseltamivir compound having the chemical formula:

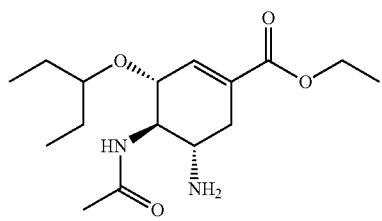 [SMILES: CCOC(=O)C1=C[C@@H](OC(CC)CC)[C@H](NC(C)=O)[C@@H](N)C1]

with an acyl hydroximoyl chloride, in an organic solvent at room temperature, to form said compound.

5. A method according to claim 4, wherein the organic solvent is a dichloromethane.

6. A method for preparing a compound according to the general structural formula:

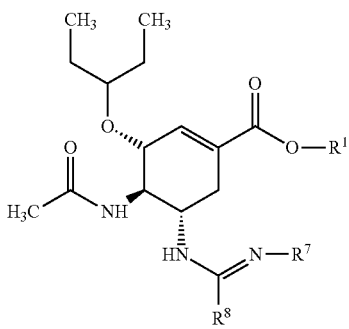

as well as the pharmaceutically acceptable salts, solvates, R/S enantiomers and/or prodrugs thereof, wherein
$R^1$ is H, or a branched or unbranched, saturated or unsaturated, substituted or unsubstituted hydrocarbon chain having a chain length of 1 to 12,
$R^7$ is H or OH,
$R^8$ is H, $R^9$, $NH_2$, $NHR^9$, $N(R^9)_2$ or $NHCOOR^1$,
$R^9$ is a branched or unbranched, substituted or unsubstituted, alkyl having a chain length of 1 to 4 carbon atoms
wherein substituents for $R^1$ and $R^9$ are selected from the group consisting of fluorine, chlorine, bromine, iodine, oxygen, sulfur, alkoxy, acyloxy, hydroxyl, mercapto, cyano, nitro, or thio alkoxy group, and a functionality which is blocked with a protecting group,
comprising reacting (3R,4R,5S)-4-acetamido-5-amino-3-(1-ethylpropoxy)cyclohex-1-en-1-carboxylic acid ethyl ester with cyanogen bromide in an organic solvent at room temperature to form a cyanamide derivative of the compound, and reacting the cyanamide derivative compound with hydroxylamine in dioxane at room temperature to form the compound.

7. A method for preparing an influenza neuraminidase inhibitor according to the general structural formula

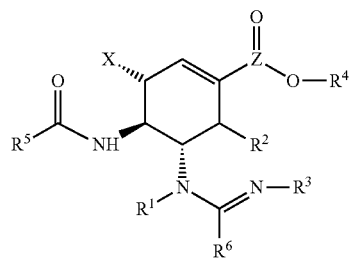

as well as the pharmaceutically acceptable salts, solvates, R/S enantiomers, or prodrugs thereof, wherein
$R^1$, $R^4$ and $R^5$ may be identical or different and is hydrogen, or a branched or unbranched, saturated or unsaturated, substituted or unsubstituted hydrocarbon chain having a chain length of 1 to 12,
$R^2$ is H
$R^3$ is H, OH, or $OR^1$
$R^6$ is H, $R^1$, $NH_2$, $NHR^1$, $N(R^1)_2$, $NHCOOR^1$,
X is $OR^1$
Z is C and
wherein substituents for $R^1$ are selected from the group consisting of fluorine, chlorine, bromine, iodine, oxygen, sulfur, alkoxy, acyloxy, hydroxyl, mercapto, cyano, nitro or thio alkoxy group, and a functionality which is blocked with a protecting group, comprising reacting an oseltamivir compound having the chemical formula:

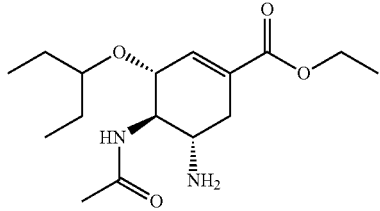 [SMILES: CCOC(=O)C1=C[C@@H](OC(CC)CC)[C@H](NC(C)=O)[C@@H](N)C1]

with an acyl hydroximoyl chloride, in an organic solvent at room temperature, to form said compound.

8. A method according to claim 7, wherein the organic solvent is a dichloromethane.

9. A method according to claim 7, wherein the oseltamivir compound is an amidoxime with $R^3$ is OH.

10. A method for preparing an influenza neuraminidase inhibitor according to the general structural formula:

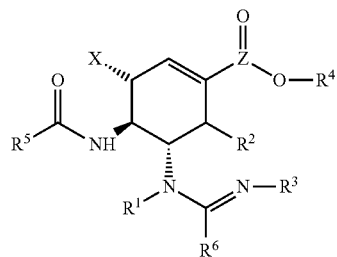

as well as the pharmaceutically acceptable salts, solvates, R/S enantiomers, or prodrugs thereof, wherein
  $R^1$, $R^4$ and $R^5$ may be identical or different and is hydrogen, a branched or unbranched, saturated or unsaturated, substituted or unsubstituted hydrocarbon chain having a chain length of 1 to 12,
  $R^2$ is H
  $R^3$ is H, OH, or $OR^1$
  $R^6$ is H, $R^1$, $NH_2$, $NHR^1$, $N(R^1)_2$, $NHCOOR^1$,
  X is $OR^1$
  Z is C and
  wherein substituents for $R^1$ are selected from the group consisting of fluorine, chlorine, bromine, iodine, oxygen, sulfur, alkoxy, acyloxy, hydroxyl, mercapto, cyano, nitro or thio alkoxy group, and a functionality which is blocked with a protecting group comprising reacting (3R,4R,5S)-4-acetamido-5-amino-3-(1-ethylpropoxy)cyclohex-1-en-1-carboxylic acid ethyl ester with cyanogen bromide in an organic solvent at room temperature to form a cyanamide derivative of the compound, and reacting the cyanamide compound with hydroxylamine in dioxane at room temperature to form the compound.

11. A method according to claim 10, wherein $R^6$ is $NH_2$, $NHR^1$ or $N(R^1)_2$, and $R^3$ is OH.

12. The method of claim 4, wherein the compound is amidoxime (3R,4R,5S)-4-Acetamido-5-[N—(N'-hydroxy)acetimidamido]-3-(1-ethylpropoxy) cyclohex-1-en-1-carboxylic acid ethyl ester, or hydroxyguanidine (3R,4R,5S)-4-acetamido-5-[N—(N'hydroxy)-guanidino]-3-(1-ethylpropoxy)cyclohex-1-en-1-carboxylic acid ethyl ester, or (3R,4R,5S)-4-acetamido-5-(N-acetimidamido)-3-(1-ethylpropoxy)cyclohex-1-en-1-carboxylic acid, or (3R,4R,5S)-4-acetamido-5-(N-guanidino)-3-(1-ethylpropoxy)cyclohex-1-en-1-carboxylic acid and/or pharmaceutically acceptable salts, solvates, R/S enantiomers and/or prodrugs thereof.

13. The method of claim 7, wherein the inhibitor is amidoxime (3R,4R,5S)-4-acetamido-5-[N—(N'-hydroxy)acetimidamido]-3-(1-ethylpropoxy)cyclohex-1-en-1-carboxylic acid ethyl ester, or hydroxyguanidine (3R,4R,5S)-4-acetamido-5-[N—(N'hydroxy)guanidino]-3-(1-ethylpropoxy) cyclohex-1-en-1-carboxylic acid ethyl ester, or (3R,4R,5S)-4-acetamido-5-(N-acetimidamido)-3-(1-ethylpropoxy)cyclohex-1-en-1-carboxylic acid, or (3R,4R,5S)-4-acetamido-5-(N-guanidino)-3-(1-ethylpropoxy) cyclohex-1-en-1-carboxylic acid as well as pharmaceutically acceptable salts, solvates or prodrugs thereof.

* * * * *